(12) United States Patent
Lin et al.

(10) Patent No.: US 10,398,896 B2
(45) Date of Patent: Sep. 3, 2019

(54) DESENSITIZING DEVICE

(71) Applicant: GiMer Medical Co., Ltd., New Taipei (TW)

(72) Inventors: Wei-Tso Lin, New Taipei (TW); Chen-Tun Wu, New Taipei (TW); Chan-Yi Cheng, New Taipei (TW); Chi-Heng Chang, New Taipei (TW)

(73) Assignee: GIMER MEDICAL CO., LTD., New Taipei (TW)

( * ) Notice: Subject to any disclaimer, the term of this patent is extended or adjusted under 35 U.S.C. 154(b) by 160 days.

(21) Appl. No.: 15/163,503

(22) Filed: May 24, 2016

(65) Prior Publication Data
US 2016/0263378 A1    Sep. 15, 2016

Related U.S. Application Data

(63) Continuation-in-part of application No. 13/949,246, filed on Jul. 24, 2013, now Pat. No. 9,370,652.

(51) Int. Cl.
| A61N 1/36 | (2006.01) |
| A61N 1/04 | (2006.01) |
| A61F 5/41 | (2006.01) |
| A61N 1/05 | (2006.01) |
| A61H 19/00 | (2006.01) |

(52) U.S. Cl.
CPC ............ *A61N 1/36014* (2013.01); *A61F 5/41* (2013.01); *A61H 19/00* (2013.01); *A61N 1/0456* (2013.01); *A61N 1/0484* (2013.01); *A61N 1/0521* (2013.01); *A61N 1/36007* (2013.01); *A61N 1/36021* (2013.01); *A61F 2005/418* (2013.01);
(Continued)

(58) Field of Classification Search
CPC .................................................. A61N 1/36014
See application file for complete search history.

(56) References Cited

U.S. PATENT DOCUMENTS

| 5,192,271 A | 3/1993 | Kalb et al. | |
| 5,540,735 A * | 7/1996 | Wingrove | .......... A61N 1/36021 602/21 |

(Continued)

FOREIGN PATENT DOCUMENTS

| CN | 1048501 A | 1/1991 |
| CN | 1138829 A | 12/1996 |

(Continued)

OTHER PUBLICATIONS

Chang et al., "Feasibility Study of Implantable Pulsed-Radiofrequency Stimulator with Verification on Sciatica Rat Model," Institute of Biomedical Engineering National Taiwan University, 2009, 2 pages.

*Primary Examiner* — Joseph M Dietrich
(74) *Attorney, Agent, or Firm* — Muncy, Geissler, Olds & Lowe, P.C.

(57) ABSTRACT

The desensitizing device contains an electrical stimulation member optionally configured on a support member. The electrical stimulation member contains a control circuit and at least two electrodes. The control circuit generates a stimulating current to the electrodes. By configuring the electrodes contacted with the skin, the stimulating signal produced by the control circuit is conducted to the electrodes and provides a subcutaneous nerve stimulation through the skin. The subcutaneous nerve is as such temporarily numbed and desensitized.

17 Claims, 26 Drawing Sheets

(52) U.S. Cl.
CPC .............. *A61H 19/32* (2013.01); *A61H 19/50* (2013.01); *A61H 2201/10* (2013.01)

(56) References Cited

U.S. PATENT DOCUMENTS

| | | |
|---|---|---|
| 5,571,118 A | 11/1996 | Boutos |
| 6,015,393 A | 1/2000 | Hovland et al. |
| 2005/0222635 A1 | 10/2005 | Krakovsky |
| 2007/0287937 A1 | 12/2007 | Suzuki et al. |
| 2009/0171144 A1 | 7/2009 | Squicciarini |
| 2010/0137938 A1* | 6/2010 | Kishawi ............... A61N 1/0551 607/46 |
| 2013/0116742 A1 | 5/2013 | Lavoisier |

FOREIGN PATENT DOCUMENTS

| | | |
|---|---|---|
| CN | 101610810 A | 12/2009 |
| CN | 202724225 U | 2/2013 |
| CN | 203469232 U | 3/2014 |
| EP | 3020448 A1 | 5/2016 |
| GB | 2499585 A | 8/2013 |
| WO | WO 95/19804 | 7/1995 |
| WO | WO 96/20753 | 7/1996 |
| WO | WO2005/007029 | 1/2005 |
| WO | WO2005/053790 A1 | 6/2005 |
| WO | WO2008/088985 A2 | 7/2008 |
| WO | WO 2008/094345 A1 | 8/2008 |
| WO | WO 2009/064641 A1 | 5/2009 |
| WO | WO2013/074809 A1 | 5/2013 |

\* cited by examiner

DESENSITIZING DEVICE

CROSS REFERENCE TO RELATED APPLICATIONS

This application is a Continuation-In-Part of U.S. application Ser. No. 13/949,246 filed on Jul. 24, 2013.

BACKGROUND

Technical Field

The present invention is generally related to desensitizing devices, and more particular to a device to reduce the sensitivity of a subcutaneous nerve by providing electrical stimulation.

Related Art

In today's busy society, people's stress significantly affects their private lives. To make the sexual activity more fulfilling, a lot of sex toys are on the market to maintain and enhance people's interest and delight.

One common sex toy is the vibrator. However, a vibrator can only provide stimulation in the tactile sense, and has little effect on the male staying power, which is a major factor in satisfying intercourse.

To promote male endurance, there are also various medications on the market. However, these medications often contain intoxicant or harmful components, and usually cause undesirable side effects.

SUMMARY

Therefore, a desensitizing device is provided herein, which contains an electrical stimulation member. The electrical stimulation member is optionally configured on a support member. The electrical stimulation member contains a control circuit, and at least two electrodes. The control circuit produces a stimulating signal. The electrodes are configured to be attached to a user's skin and electrically connected to the control circuit to receive the simulating signal from the control circuit and to apply the stimulating signal to a subcutaneous nerve via the skin. The stimulating signal make the electrodes generate an electric field at least partially covering the subcutaneous nerve, and the magnitude of the electric field ranges from 100 V/m to 1000 V/m. When the simulating signal is applied, the subcutaneous nerve is temporarily desensitized to ease the neuralgia.

By applying the support member to the male genital, the electrodes will be in contact with the penis skin, the stimulating signal produced by the control circuit can then be conducted via the electrodes and provides a low-strength subcutaneous nerve stimulation through the penis skin. The subcutaneous nerve of the male genital is then numbed and desensitized temporarily, thereby prolonging the erection state of male genitals during intercourse. Since no medication is involved, no undesirable side effects from the medicine could take place.

In another scenario, the electrodes can also be applied to or near the body parts which suffers from pain. For example, if a user presents rheumatism at his/her elbow, he/she can apply the electrodes on the neural pathway between the spinal cord and his/her elbow. If a user has an episode of migraine, he/she can apply the electrodes on the neural pathway between the spinal cord and his/her forehead or temples to ease the pain.

In one embodiment, the stimulating signal is a pulse signal having a frequency between 200 KHz and 800 KHz.

In one embodiment, the frequency of the stimulating signal ranges from 200 KHz to 450 KHz, or ranges from 450 KHz to 550 KHz, or ranges from 550 KHz to 800 KHz.

In one embodiment, the voltage of the stimulating signal ranges from −10V to −1V or ranges from 1V to 10V.

In one embodiment, the current of the stimulating signal ranges from 2 mA to 50 mA.

In one embodiment, the stimulation signal is adapted to block the neurotransmission of the subcutaneous nerve.

In one embodiment, the subcutaneous nerve is under the skin of a penis, a wrist, an elbow, or a head.

In one embodiment, the support member has an outer circumference, an inner circumference, a through channel surrounded by the inner circumference, and an accommodation space with a first opening on the outer circumference and at least two second openings on the inner circumference.

In one embodiment, the at least two electrodes are exposed from the inner circumference through the second openings, respectively.

In one embodiment, the at least two electrodes are flexible pads.

In one embodiment, the support member is belt-shaped or a substantially ring-like shape.

In one embodiment, the desensitizing device further includes a power supply unit.

In one embodiment, the power supply unit includes a removable battery.

In one embodiment, the power supply unit includes a built-in rechargeable battery.

Another perspective of the present invention is to provide a desensitizing method for a desensitizing device having a control circuit configured, and at least two electrodes configured to be attached to a user's skin and electrically connected to the control circuit. The desensitizing method includes steps of: producing a stimulating signal using the control circuit; receiving the stimulating signal by the at least two electrodes; and applying the stimulating signal to a subcutaneous nerve via the skin. The stimulating signal makes the at least two electrodes generate an electric field at least partially covering the subcutaneous nerve, and the magnitude of the electric field ranges from 100 V/m to 1000 V/m such that when the simulating signal is applied, the subcutaneous nerve is temporarily desensitized.

In one embodiment, the stimulating signal is a pulse signal having a frequency between 200 KHz and 800 KHz.

In one embodiment, the voltage of the stimulating signal ranges from −10V to −1V or ranges from 1V to 10V, and the current of the stimulating signal ranges from 2 mA to 50 mA.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become apparent to those versed in the art upon making reference to the detailed description and the accompanying sheets of drawings in which a preferred structural embodiment incorporating the principles of the present invention is shown by way of illustrative example.

BRIEF DESCRIPTION OF THE DRAWINGS

The embodiments will become more fully understood from the detailed description and accompanying drawings, which are given for illustration only, and thus are not limitative of the present invention, and wherein.

DETAILED DESCRIPTION OF THE INVENTION

Figure 1:
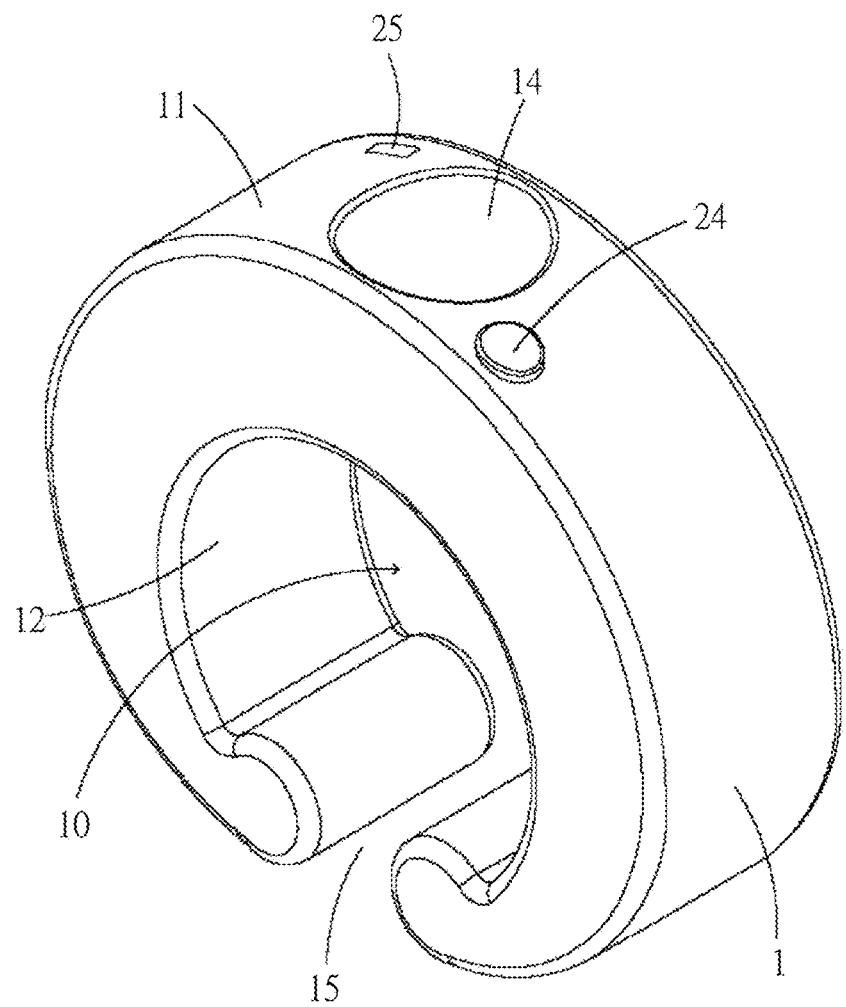
FIG. 1 is a perspective diagram showing a desensitizing device according to a first embodiment of the present invention.
Figure 2:
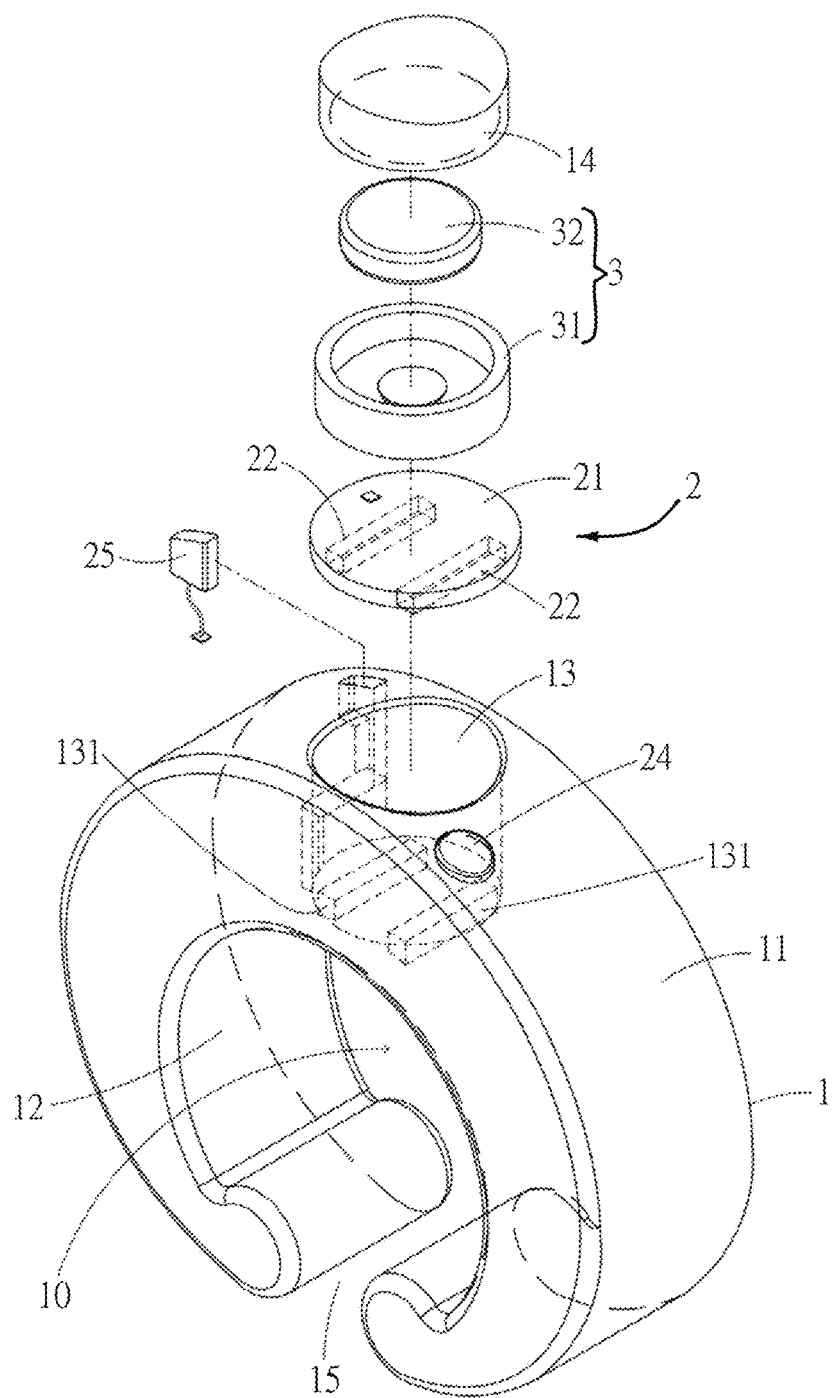
FIG. 2 is a perspective break-down diagram showing the various components of the desensitizing device of FIG. 1.
Figure 3:
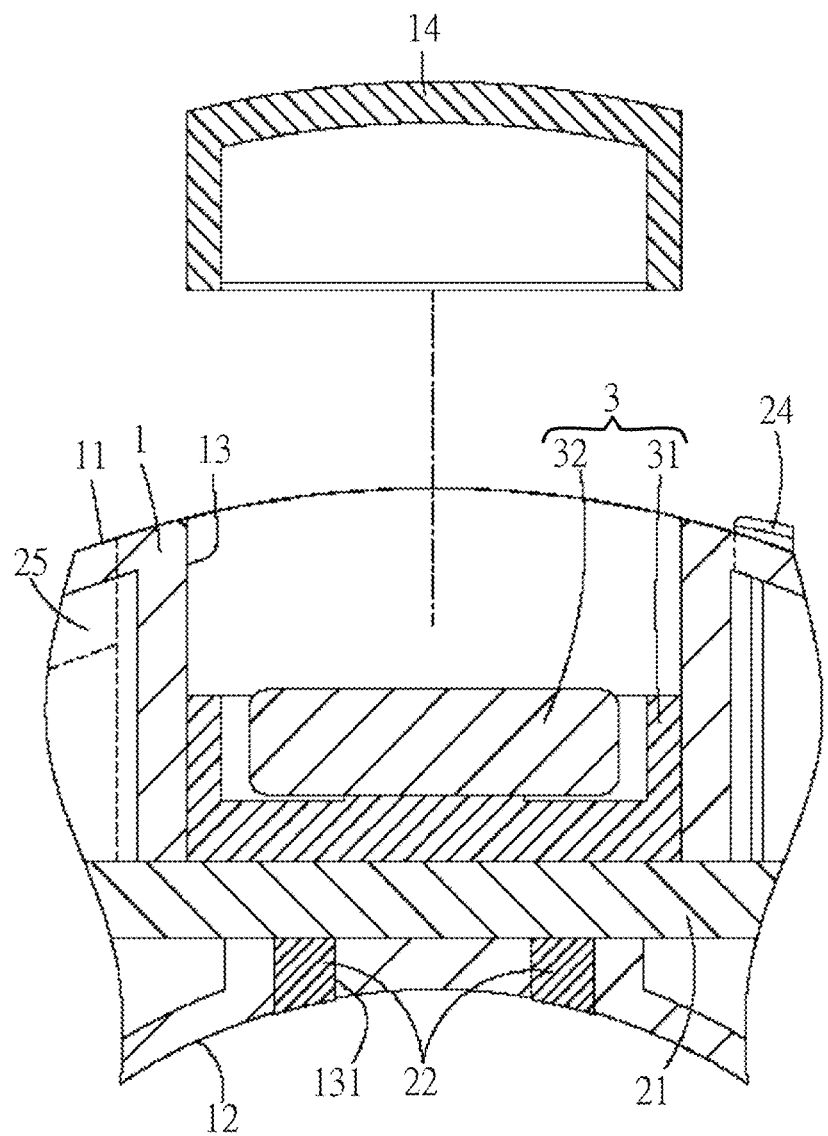
FIG. 3 is a partial sectional diagram showing the desensitizing device of FIG. 1.
Figure 4:
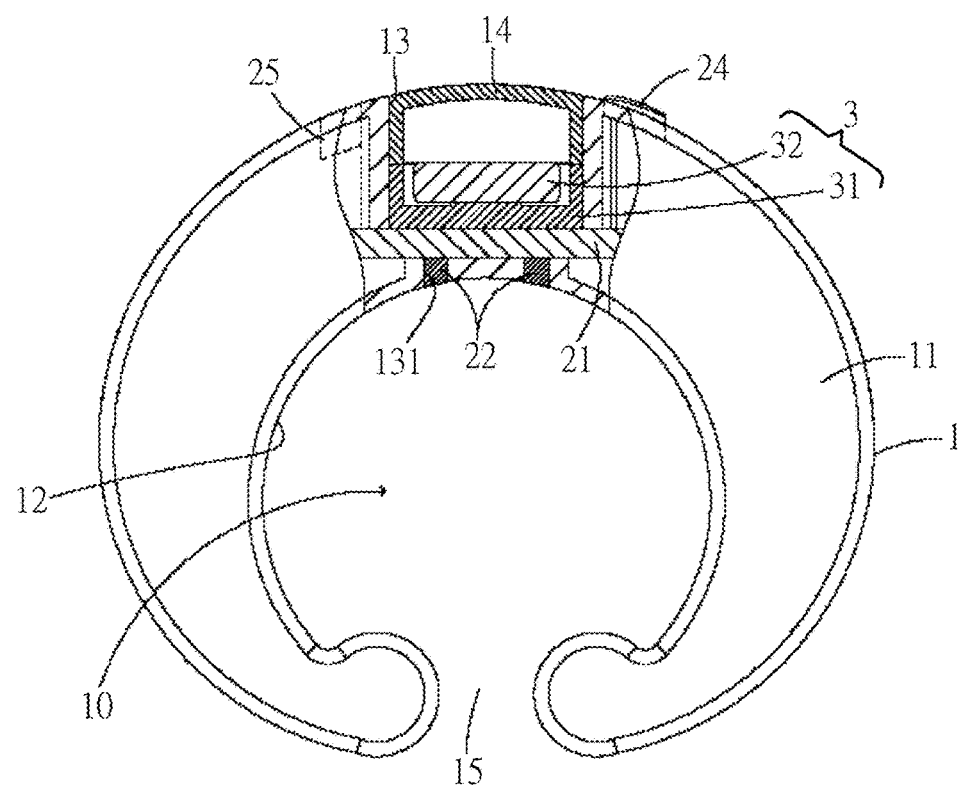
FIG. 4 is a partial sectional diagram showing the desensitizing device of FIG. 1.

The embodiments of the invention will be apparent from the following detailed description, which proceeds with reference to the accompanying drawings, wherein the same references relate to the same elements.

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

As shown in FIGS. 1 to 4, a desensitizing device according to a first embodiment of the present invention contains an electrical stimulation member 2, and a power supply unit 3. The electrical stimulation member 2 is optionally configured on a support member 1. The support member 1 can be ring-shaped or other appropriate shapes.

In the embodiment, the support member 1 has an outer circumference 11, an inner circumference 12, and a through channel 10 surrounded by the inner circumference 12. The support member 1 has an accommodation space 13 with a circular first opening on the outer circumference 11 sealed by a cover 14, and at least two linear second openings 131 on the inner circumference 12 so that the accommodation space 13 is connected to the through channel 10. The support member 1 is made of a flexible material and can be configured into a C-like shape with an axially-oriented linear opening 15 so that the linear opening 15 can be elastically broadened.

The electrical stimulation member 2 is housed in the accommodation space 13, and contains a control circuit 21, and at least two electrodes 22. The power supply unit 3 can contain a removable battery or a built-in rechargeable battery, and is electrically connected to the control circuit 21 so as to provide electricity to the control circuit 21. In the present embodiment, the power supply unit 3 contains a removable battery 32 and a battery chamber 31. The battery chamber 31 has a positive terminal and a negative terminal, both connected to the control circuit 21. The battery 32 is accommodated in the battery chamber 31 and the battery 32's positive and negative terminals are connected to the battery chamber 31's positive and negative terminals, respectively. The electrodes 22 are electrically connected to the control circuit 21, and are exposed to the through channel 10 on the inner circumference 12 through the second openings 131, respectively. With the electricity provided by the power supply unit 3, the control circuit 21 generates and delivers a stimulating current to the electrodes 22.

The stimulating current produced by the control circuit 21 can be a high-frequency signal between 200 KHz and 800 KHz, or a low-frequency signal between 0.5 Hz and 1 KHz (preferably between 2 Hz and 30 Hz), or a mixed signal with a high-frequency component and a low-frequency component, wherein the high-frequency component of the mixed signal is between 200 KHz and 800 KHz, and the low-frequency component of the mixed signal is between 0.5 Hz and 1 KHz (preferably between 2 Hz and 30 Hz). The high-frequency or low-frequency signal of the stimulating current can be a continuous wave or a train of pulses. The wave can be a sinusoidal wave, a triangular wave, a square wave, or one with an appropriately shaped waveform.

As the electrical stimulation member 2 is accommodated in the accommodation space 13, the control circuit 21 can be placed on a bottom side of the accommodation space 13. The electrodes 22 are electrically connected to a bottom side of the control circuit 21, configured in the second openings 131, respectively, and exposed from the inner circumference 12. The power supply unit 3 has the battery chamber 31 electrically connected to a top side of the control circuit 21, and the battery 32 is placed in the battery chamber 31. The first opening of the accommodation space 13 is then sealed by the cover 14 so that the electrical stimulation member 2 is tightly housed in the accommodation space 13.

The electrical stimulation member 2 further contains a switch 24 and an indicator lamp 25. The switch 24 is electrically connected to the control circuit 21 for turning the control circuit 21 on and off, and is exposed from the outer circumference 11 on the support member 1. The indicator lamp 25 is also electrically connected to the control circuit 21 and is exposed from the outer circumference 11 on the support member 1.

By threading a male genital through the through channel 10 of the support member 1 so that the electrodes 22 are in contact with the penis skin, the stimulating current produced by the control circuit 21 when the electrical stimulation member 2 is turned on is conducted by the electrodes 22 and provides a low-strength subcutaneous nerve stimulation through the penis skin. The subcutaneous nerve is as such temporarily numbed and desensitized, thereby enhancing the staying power of male genitals during intercourse. Since no medication is employed, potential undesirable side effects are avoided.

Figure 5:
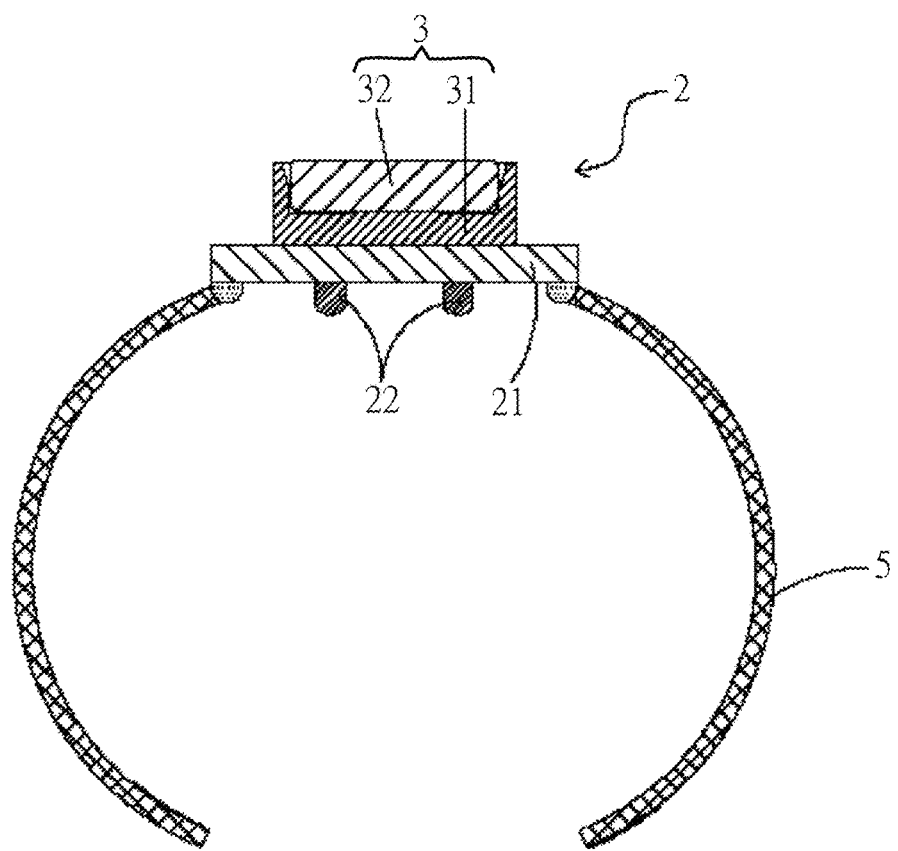
FIG. 5 is a sectional diagram showing a desensitizing device according to a second embodiment of the present invention.

FIG. 5 depicts a second embodiment of the present invention. As illustrated, a desensitizing device of the present embodiment has an electrical stimulation member 2 configured on a belt-like support member 5. The support member 5 girdles a male genital so that the electrodes 22 of the electrical stimulation member 2 are in contact with the penis skin. The stimulating current produced by the control circuit 21 is conducted to the electrodes 22 and provides a low-strength subcutaneous nerve stimulation through the penis skin. The subcutaneous nerve is as such temporarily numbed and desensitized.

Figure 6:
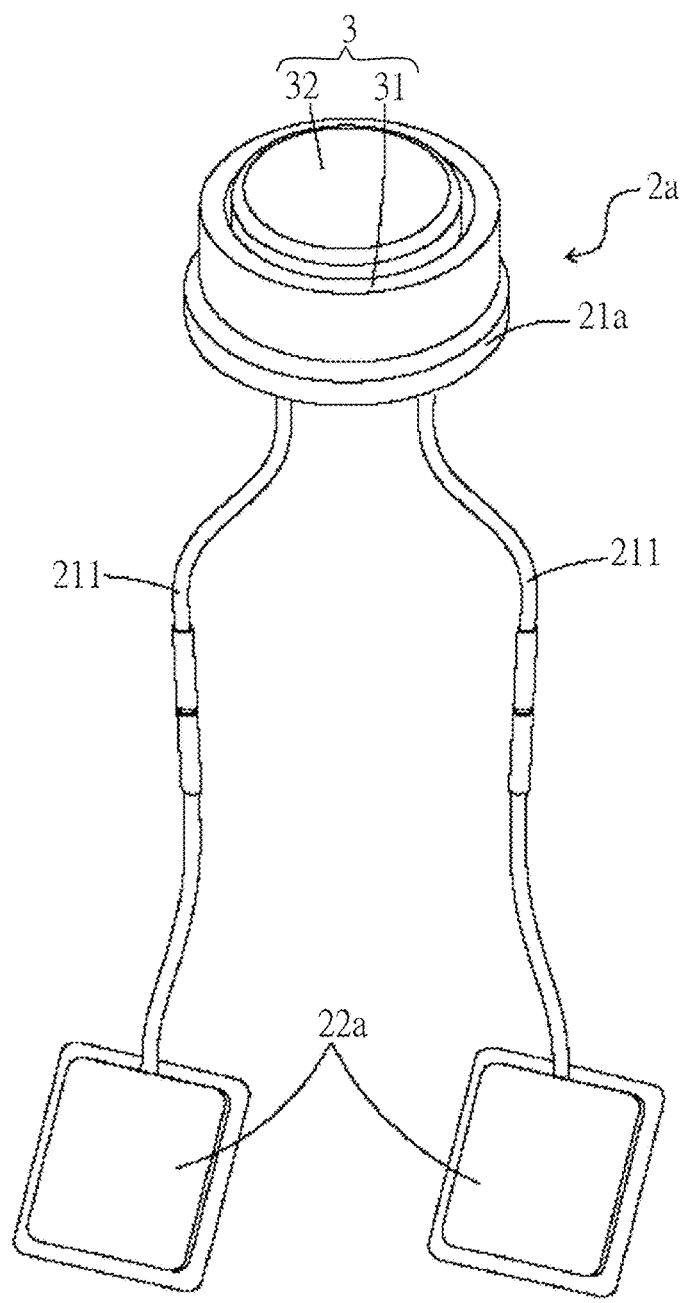
FIG. 6 is a perspective diagram showing a desensitizing device according to a third embodiment of the present invention.

FIG. 6 depicts a third embodiment of the present invention. As illustrated, a desensitizing device of the present embodiment has an electrical stimulation member 2a that is applied independently without a support member or a power supply unit. In the embodiment, the two electrodes 22a of the control circuit 21a are configured in two flexible pads and extended by two transmission wires 211 so that the electrodes 22a can be attached to the penis skin directly. The stimulating current produced by the control circuit 21a is conducted to the electrodes 22a and provides a low-strength subcutaneous nerve stimulation through the skin. The subcutaneous nerve is as such temporarily numbed. In addition, the high-frequency simulating signal produced by the control circuit 21a can also be applied to other body parts (e.g., a wrist, an elbow, a head etc.) for low-strength subcutaneous nerve stimulation. In these applications, the electrodes 22a are attached directly to the desired body part. The stimulating signal produced by the control circuit 21a is conducted to the electrodes 22a and provides a low-strength subcutaneous nerve stimulation through the skin of the desired body part. The subcutaneous nerve is thereby temporarily numbed and desensitized so as to ease the neuralgia.

Please note that, the term "stimulating signal" used herein to refer to an electrical signal including voltage signal or current signal which can cause the electrodes 22a to generate an electric field. Reference to a particular type of electrical signal as being a stimulating signal is not intended to limit the scope of the claims unless a particular type of electrical signal is recited in the claims.

The stimulation signal is adapted to block the neurotransmission of the subcutaneous nerve. For example, if the stimulation signal is a voltage signal, the stimulating signal ranges from −10V to −1V or ranges from 1V to 10V. If the stimulation signal is a current signal, the stimulation signal ranges from 2 mA to 50 mA. For example, the stimulation signal is a voltage signal whose magnitude is 5V, or the stimulation signal is a current signal, the stimulation signal may be a 20 mA current signal.

Considering a case that the desensitizing device is used on dorsal penile verves, the distance between any adjacent two electrodes 22a ranges from 1 mm to 7 mm, the distance between each of the electrodes 22 and the subcutaneous nerve ranges from 0 to 10 mm, and the widths of the two electrodes 22a range from 3 mm to 10 mm, thereby when generated, the electric field at least partially covers the subcutaneous nerve which conducting the pain and has a magnitude ranging from 100 V/m to 1000 V/m, wherein the subcutaneous nerve is on the nerve conduction pathway between the spinal cord and locations effected.

Considering another case that the desensitizing device is used on median verves, the distance between any adjacent two electrodes 22a ranges from 5 mm to 60 mm, the distance between each of the electrodes 22 and the subcutaneous nerve ranges from 0 to 20 mm, and the widths of the two electrodes 22a range from 2 mm to 20 mm, thereby when generated, the electric field at least partially covers the subcutaneous nerve which conducting the pain and has a magnitude ranging from 100 V/m to 1000 V/m, wherein the subcutaneous nerve is on the nerve conduction pathway between the spinal cord and locations effected.

When applying the simulating signal to the subcutaneous nerve, the frequency of the stimulating signal could range from 200 KHz to 450 KHz or from 450 KHz to 550 KHz or from 550 KHz to 800 KHz, the subcutaneous nerve is temporarily desensitized and possibly eased from neuralgia. If the selected frequency is between 200 KHz~450 KHz, device operates in relatively low frequency so it is less risky to produce biological heat for better safety. Otherwise, if the selected frequency is between 550 KHz~1000 KHz, the generated electric field has greater density so its electrical stimulation has better performance.

Figure 7:
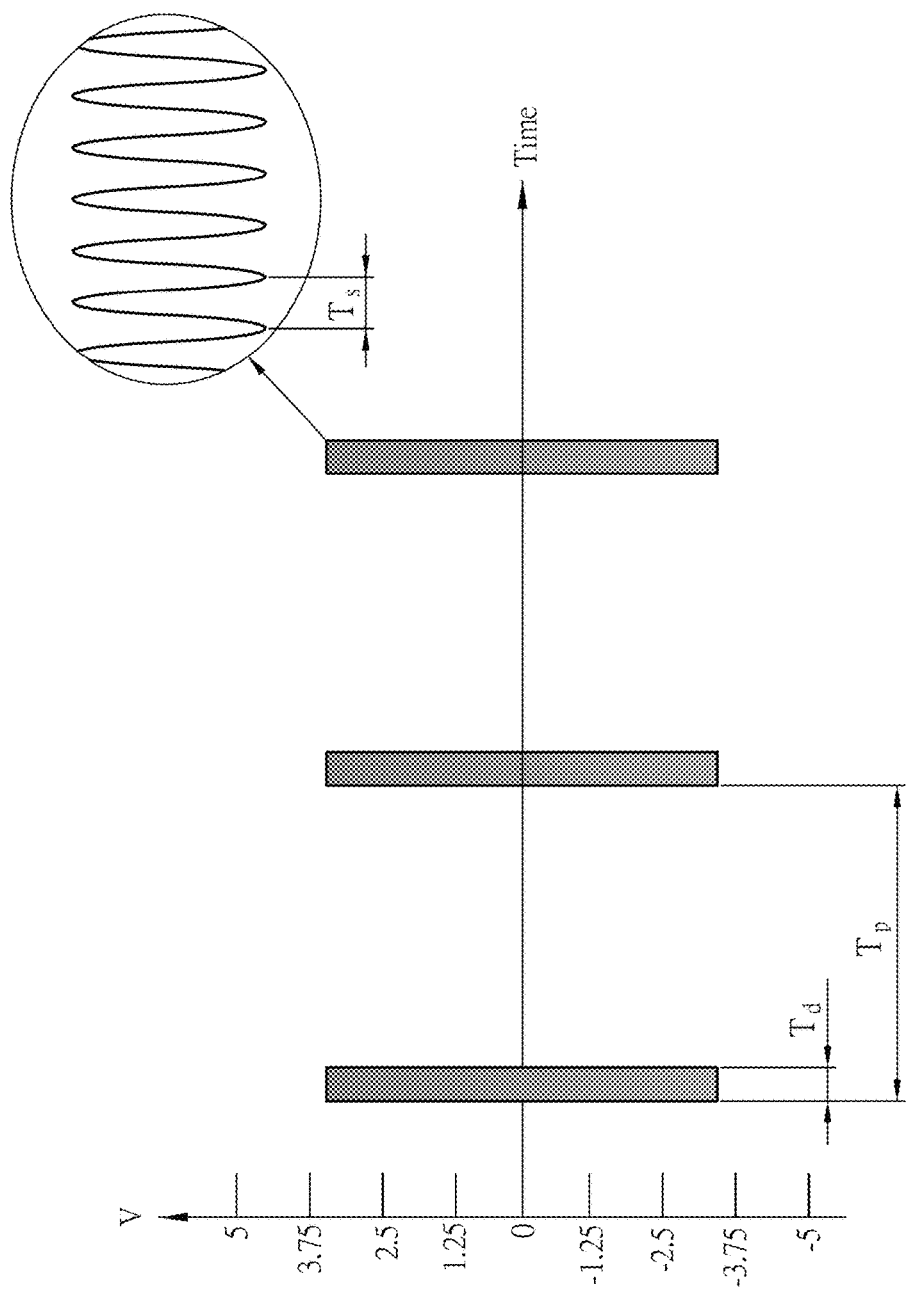
FIG. 7 is a schematic diagram showing the wave form of the stimulation signal.

In addition, please refer to FIG. 7, which is a schematic diagram showing the wave form of the stimulation signal. In the embodiment, the stimulation signal outputted from the desensitizing device may be a continuous sine wave, a continuous triangular wave or a stimulation signal of high-frequency pulse. In the embodiment, the stimulation signal is a continuous sine wave and the magnitude of the signal is between +3.5V and −3.5V and the frequency of the stimulating signal is 500 KHz (1/Ts). One pulse cycle time $T_p$ has a plurality of pulse signals and at least one period of rest time $(T_p-T_d)$. One pulse cycle time $T_p$ is the reciprocal of pulse repetition frequency. The pulse repetition frequency (also called pulse frequency) is between 0~1 KHz, preferably between 1~100 Hz. In the embodiment, the pulse repetition frequency of the stimulation signal is about 2 Hz. Besides, the duration time $T_d$ of pulses in one pulse cycle time is between 1~250 ms, preferably between 10~100 ms. In the embodiment, it is 25 ms. By adjusting an operation duration time $T_d$, the amount of the electrical stimulation is adjusted and the time for dissipating the produced biological heat accordingly. For example, if the stimulation intensity is relatively low, the duration time $T_d$ may be increased to continuously stimulate. If the stimulation intensity and the frequency are relatively high, the duration time $T_d$ may be decreased to raise the time for dissipating.

In other words, the electric field covers the subcutaneous nerve and its surroundings with low intensity, low temperature and high frequency simulating signal without damaging the neural cells of the subcutaneous nerve, thereby the biomolecular generation by the subcutaneous nerve is suppressed. Thus, the neurotransmission capability of the subcutaneous nerve in the target zone is lowered and the neurotransmission is blocked.

Figure 8:
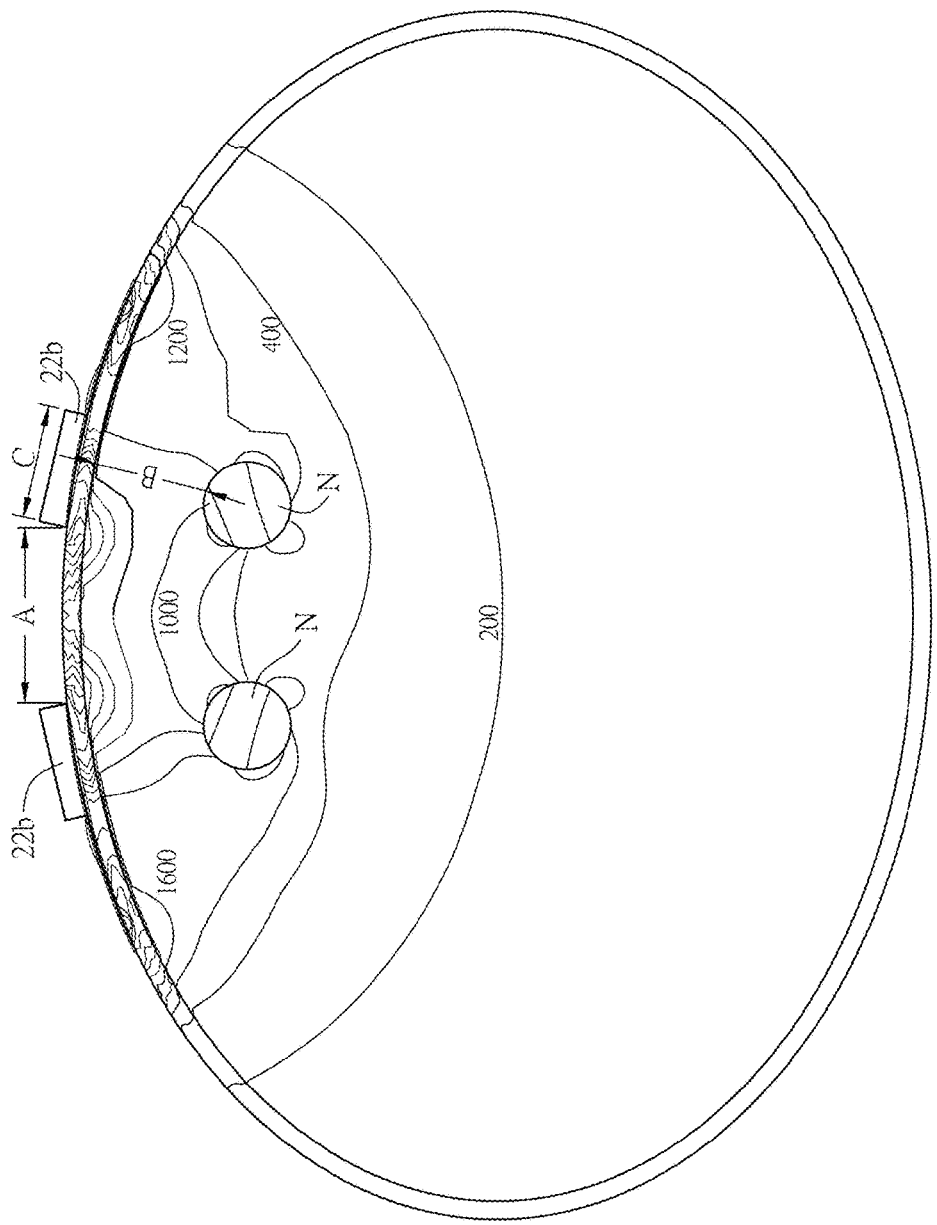
FIGS. 8-26 are schematic diagrams of the electric field simulation of the electronic stimulation device.

Furthermore, please refer to FIG. 8, which is a schematic diagram of the electric field simulation of the desensitizing device when applying on a penis. The field pattern of the electric field is adjusted by adjusting the distance A between the electrodes 22b, the distance B between skin surface and the dorsal penile nerve N (the circle portion), or the width C of the electrodes. In the simulation experiment, the voltage of the stimulating signal is 5V, the frequency of the stimulating signal is 500 KHz. As shown in the FIG. 8, within the workable distance, in the experiment the distance A=5 mm, the distance B=5 mm and the width C is 3 mm, the electric field (the strength of the electric field is 800V/m~1000V/m) may only or mainly effectively cover the subcutaneous nerve N. Relatively, the electric field strength is more intense if the position is closer to the electrodes 22b.

Figure 9:
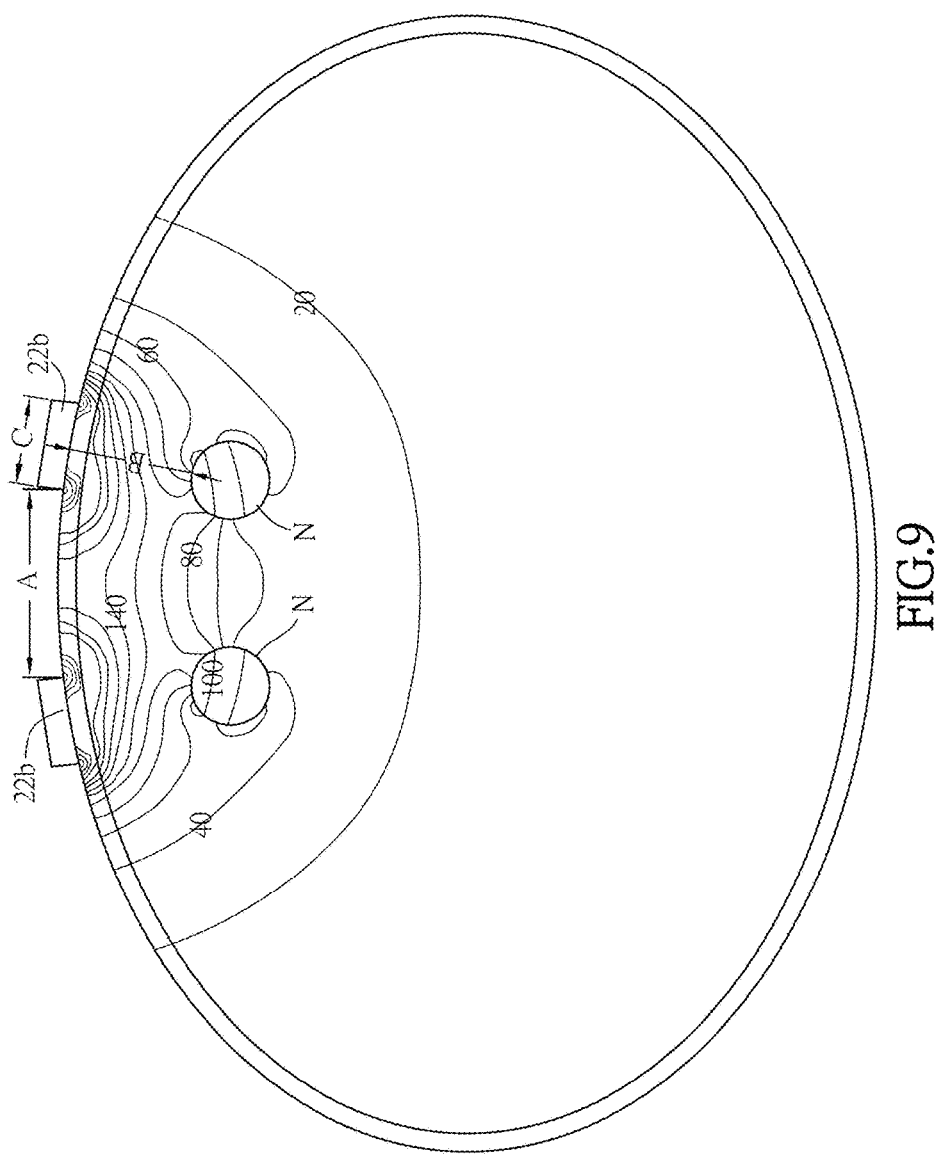

Furthermore, please refer to FIG. 9, which is another schematic diagram of the electric field simulation of the desensitizing device when applying on a penis. The field pattern of the electric field is adjusted by adjusting the distance A between the electrodes 22b, the distance B between skin surface and the dorsal penile nerve N (the circle portion), or the width C of the electrodes. In the simulation experiment, the voltage of the stimulating signal is 1V, the frequency of the stimulating signal is 800 KHz. As shown in the FIG. 9, within the workable distance, in the experiment the distance A=5 mm, the distance B=5 mm and the width C is 3 mm, the electric field (the strength of the electric field is 100V/m~120V/m) may only or mainly effectively cover the subcutaneous nerve N. Relatively, the electric field strength is more intense if the position is closer to the electrodes 22b.

Figure 10:
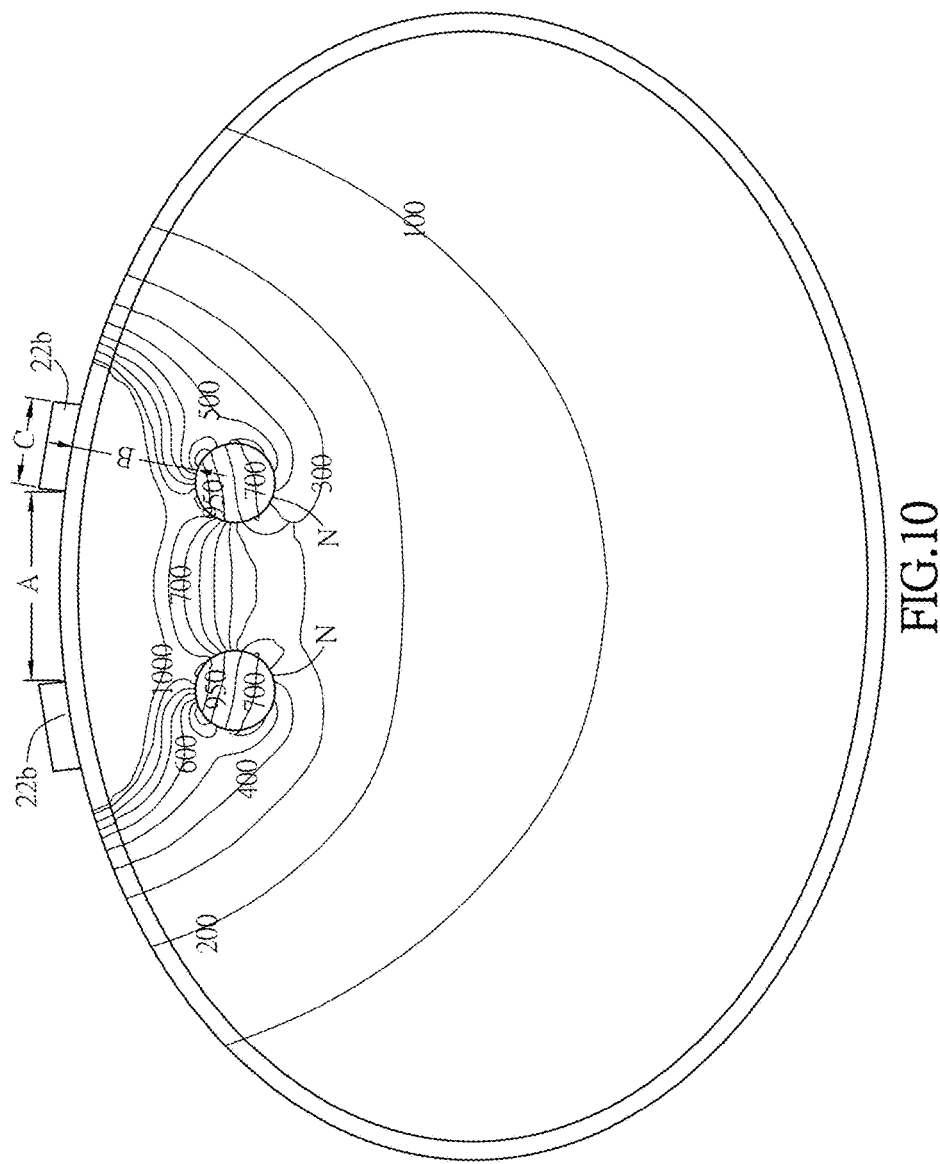

Furthermore, please refer to FIG. 10, which is yet another schematic diagram of the electric field simulation of the desensitizing device when applying on a penis. The field pattern of the electric field is adjusted by adjusting the distance A between the electrodes 22b, the distance B between skin surface and the dorsal penile nerve N (the circle portion), or the width C of the electrodes. In the simulation experiment, the voltage of the stimulating signal is 10V, the frequency of the stimulating signal is 200 KHz. As shown in the FIG. 10, within the workable distance, in the experiment the distance A=5 mm, the distance B=5 mm and the width C is 3 mm, the electric field (the strength of the electric field is 700V/m~950V/m) may only or mainly effectively cover the subcutaneous nerve N. Relatively, the electric field strength is more intense if the position is closer to the electrodes 22b.

Figure 11:
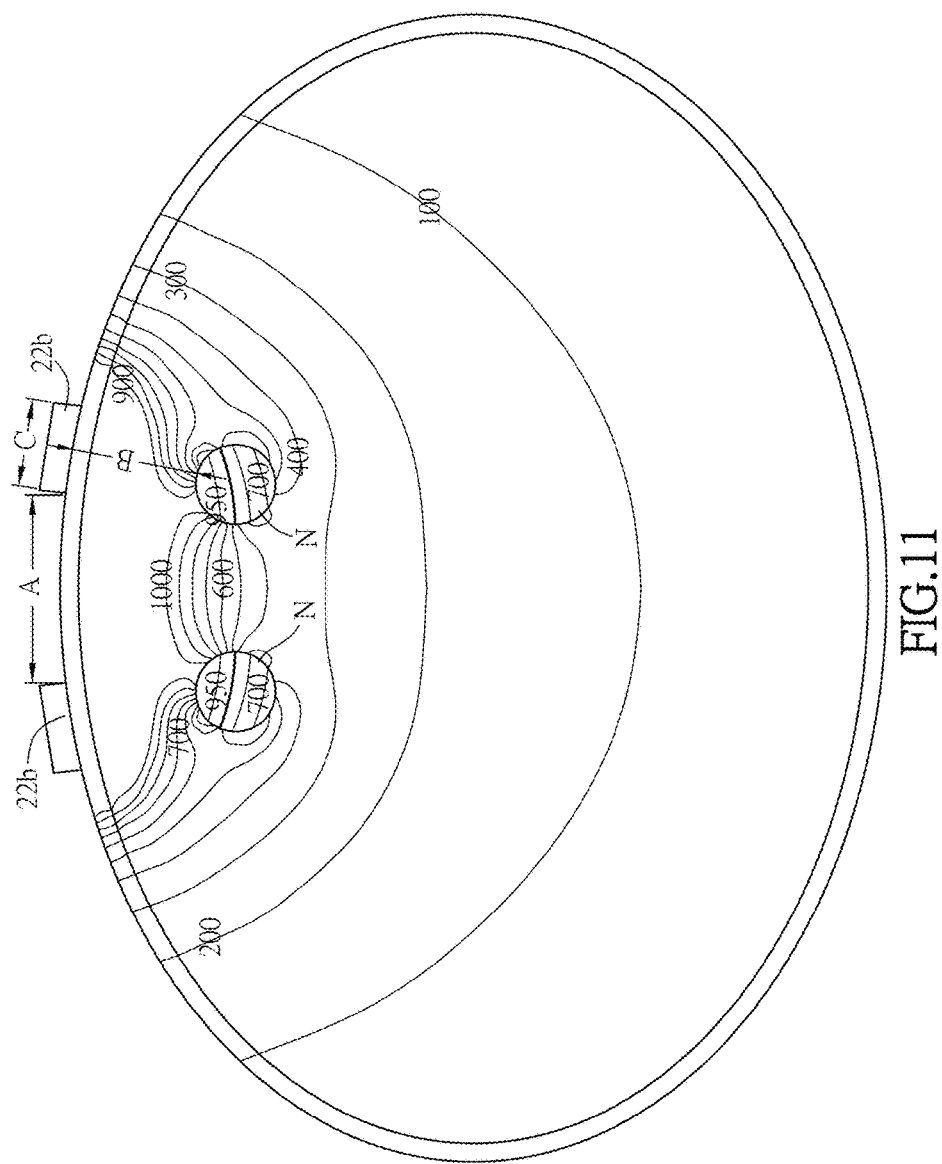

Furthermore, please refer to FIG. 11, which is yet another schematic diagram of the electric field simulation of the desensitizing device when applying on a penis. The field pattern of the electric field is adjusted by adjusting the distance A between the electrodes 22b, the distance B between skin surface and the dorsal penile nerve N (the circle portion), or the width C of the electrodes. In the simulation experiment, the voltage of the stimulating signal is 10V, the frequency of the stimulating signal is 800 KHz. As shown in the FIG. 11, within the workable distance, in the experiment the distance A=5 mm, the distance B=5 mm and the width C is 3 mm, the electric field (the strength of the electric field is 700V/m~950V/m) may only or mainly effectively cover the subcutaneous nerve N. Relatively, the electric field strength is more intense if the position is closer to the electrodes 22b.

Figure 12:
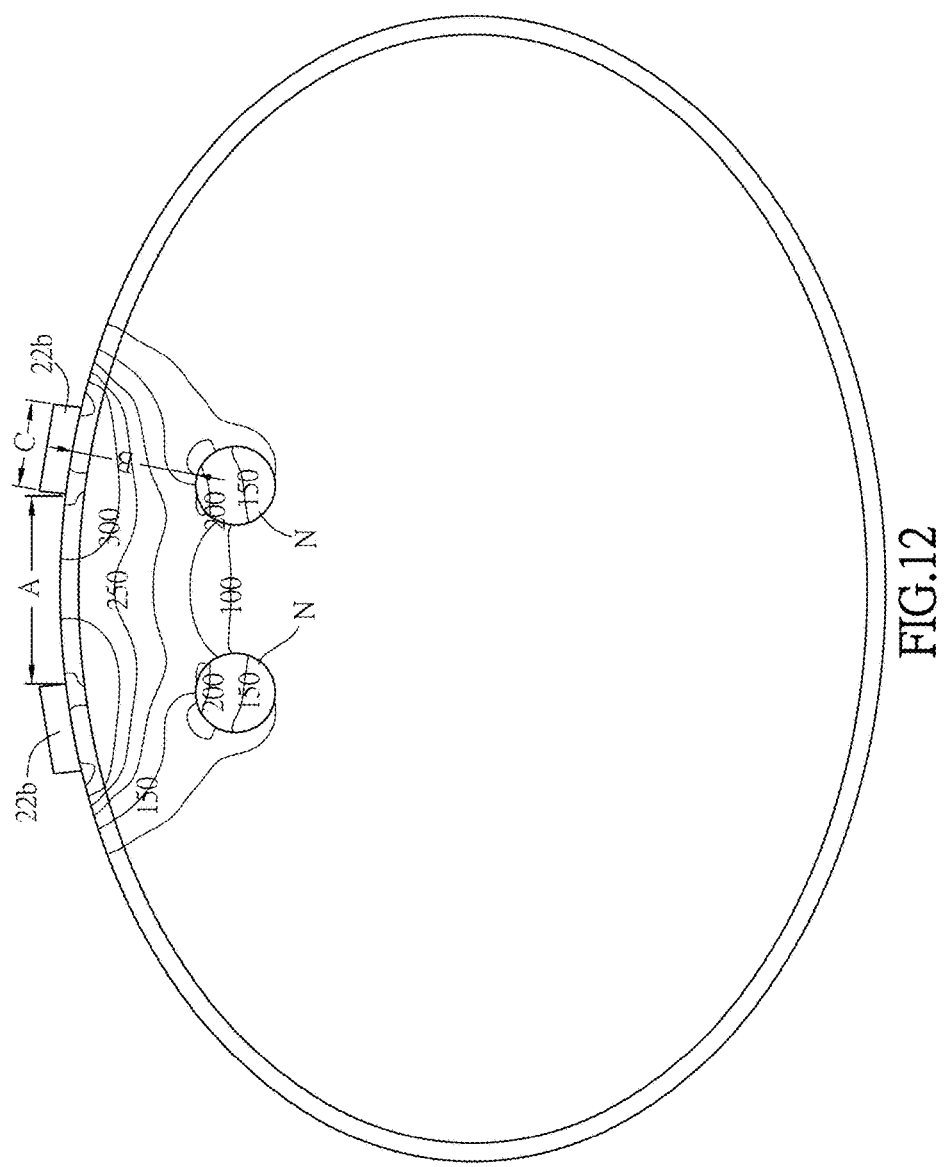

Furthermore, please refer to FIG. 12, which is yet another schematic diagram of the electric field simulation of the desensitizing device when applying on a penis. The field pattern of the electric field is adjusted by adjusting the distance A between the electrodes 22b, the distance B between skin surface and the dorsal penile nerve N (the circle portion), or the width C of the electrodes. In the simulation experiment, the voltage of the stimulating signal is 2V, the frequency of the stimulating signal is 200 KHz. As shown in the FIG. 12, within the workable distance, in the experiment the distance A=5 mm, the distance B=5 mm and the width C is 3 mm, the electric field (the strength of the electric field is 150V/m~200V/m) may only or mainly effectively cover the subcutaneous nerve N. Relatively, the electric field strength is more intense if the position is closer to the electrodes 22b.

Figure 13:
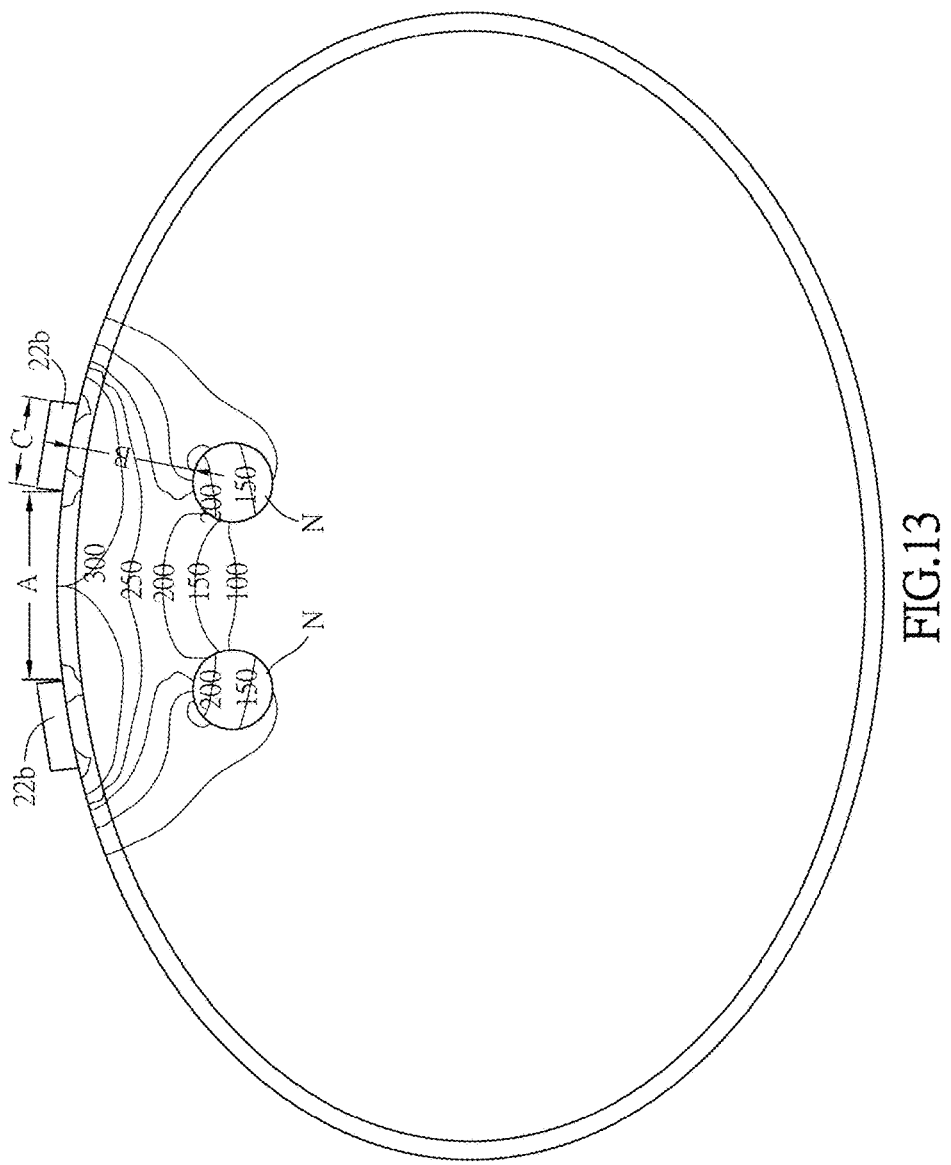

Furthermore, please refer to FIG. 13, which is yet another schematic diagram of the electric field simulation of the desensitizing device when applying on a penis. The field pattern of the electric field is adjusted by adjusting the distance A between the electrodes 22b, the distance B between skin surface and the dorsal penile nerve N (the circle portion), or the width C of the electrodes. In the simulation experiment, the voltage of the stimulating signal is 2V, the frequency of the stimulating signal is 800 KHz. As shown in the FIG. 13, within the workable distance, in the experiment the distance A=5 mm, the distance B=5 mm and the width C is 3 mm, the electric field (the strength of the electric field is 150V/m to 200V/m) may only or mainly effectively cover the subcutaneous nerve N. Relatively, the electric field strength is more intense if the position is closer to the electrodes 22b.

Figure 14:
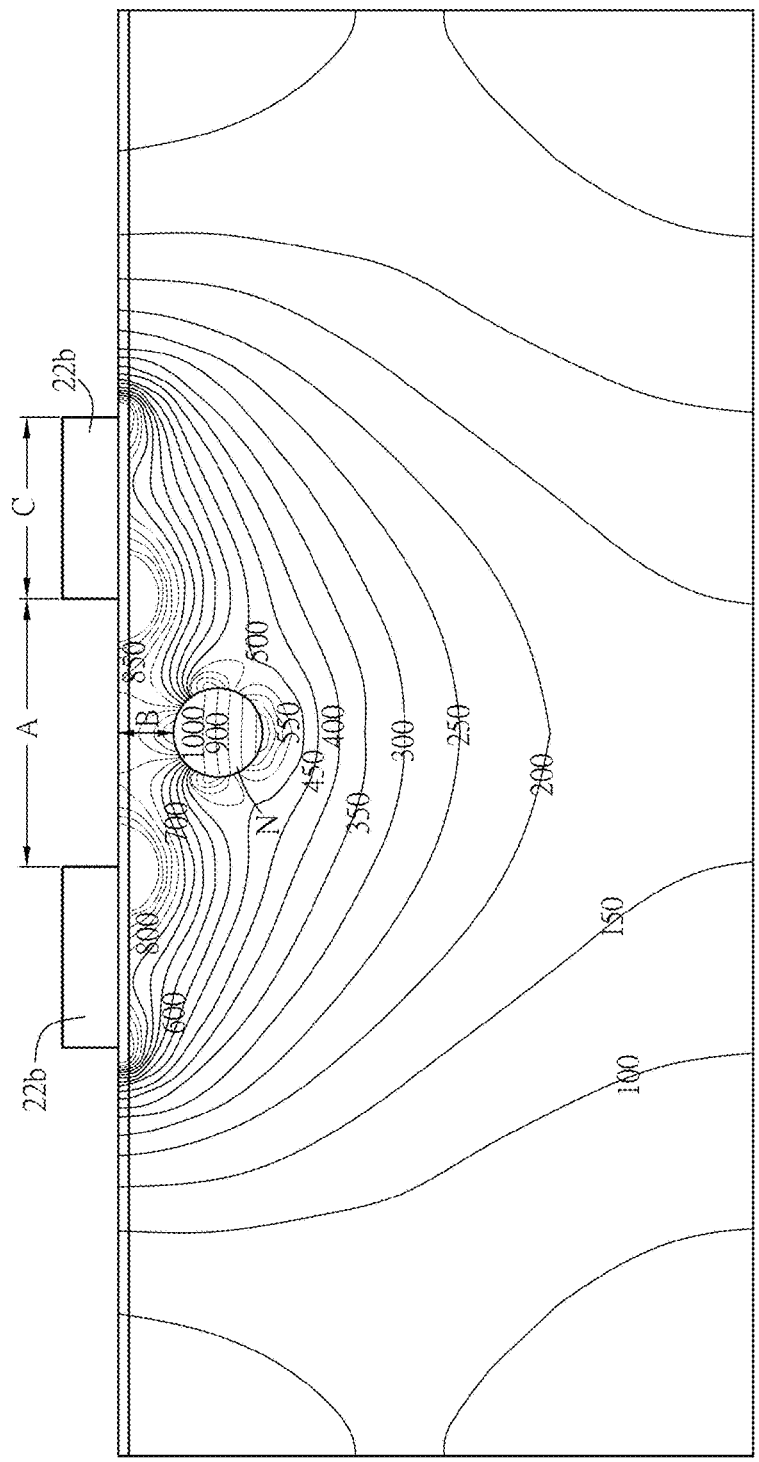

In another application of the present invention, please refer to FIG. 14, which is a schematic diagram of the electric field simulation of the desensitizing device when applying on a wrist. Please note that, in this embodiment, the electrodes 22b is favorably the flexible pads. The field pattern of the electric field is adjusted by adjusting the distance A between the electrodes 22b, the distance B between skin surface and the median nerve N (the circle portion), or the width C of the electrodes. In the simulation experiment, the voltage of the stimulating signal is 10V, the frequency of the stimulating signal is 800 KHz. As shown in the FIG. 14, within the workable distance, in the experiment the distance A=15 mm, the distance B=5 mm and the width C is 10 mm, the electric field (the strength of the electric field is 550V/m~1000V/m) may only or mainly effectively cover the subcutaneous nerve N. Relatively, the electric field strength is more intense if the position is closer to the electrodes 22b.

Figure 15:
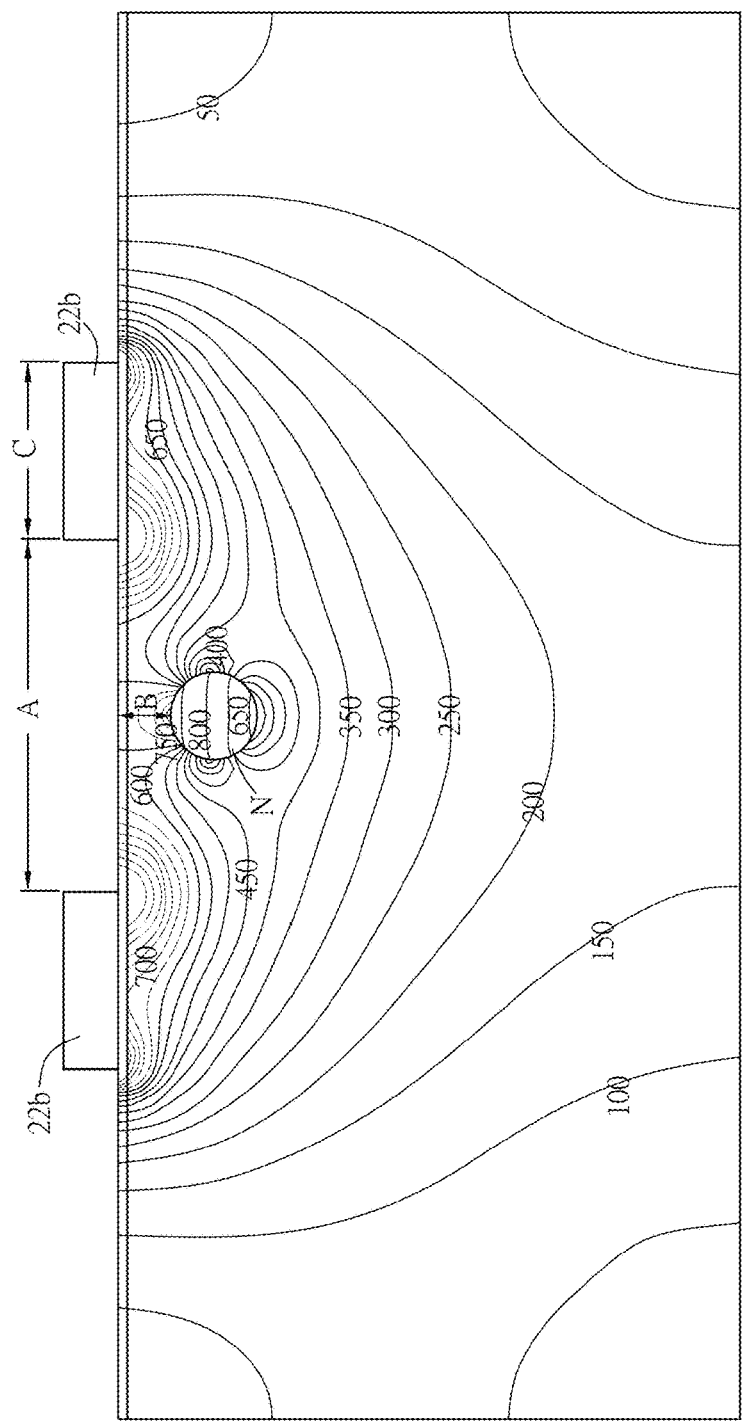

Furthermore, please refer to FIG. 15, which is yet another schematic diagram of the electric field simulation of the desensitizing device when applying on a wrist. The field pattern of the electric field is adjusted by adjusting the distance A between the electrodes 22b, the distance B between skin surface and the median nerve N (the circle portion), or the width C of the electrodes. In the simulation experiment, the voltage of the stimulating signal is 10V, the frequency of the stimulating signal is 800 KHz. As shown in the FIG. 15, within the workable distance, in the experiment the distance A=20 mm, the distance B=5 mm and the width C is 10 mm, the electric field (the strength of the electric field is 650V/m~750V/m) may only or mainly effectively cover the subcutaneous nerve N. Relatively, the electric field strength is more intense if the position is closer to the electrodes 22b.

Figure 16:
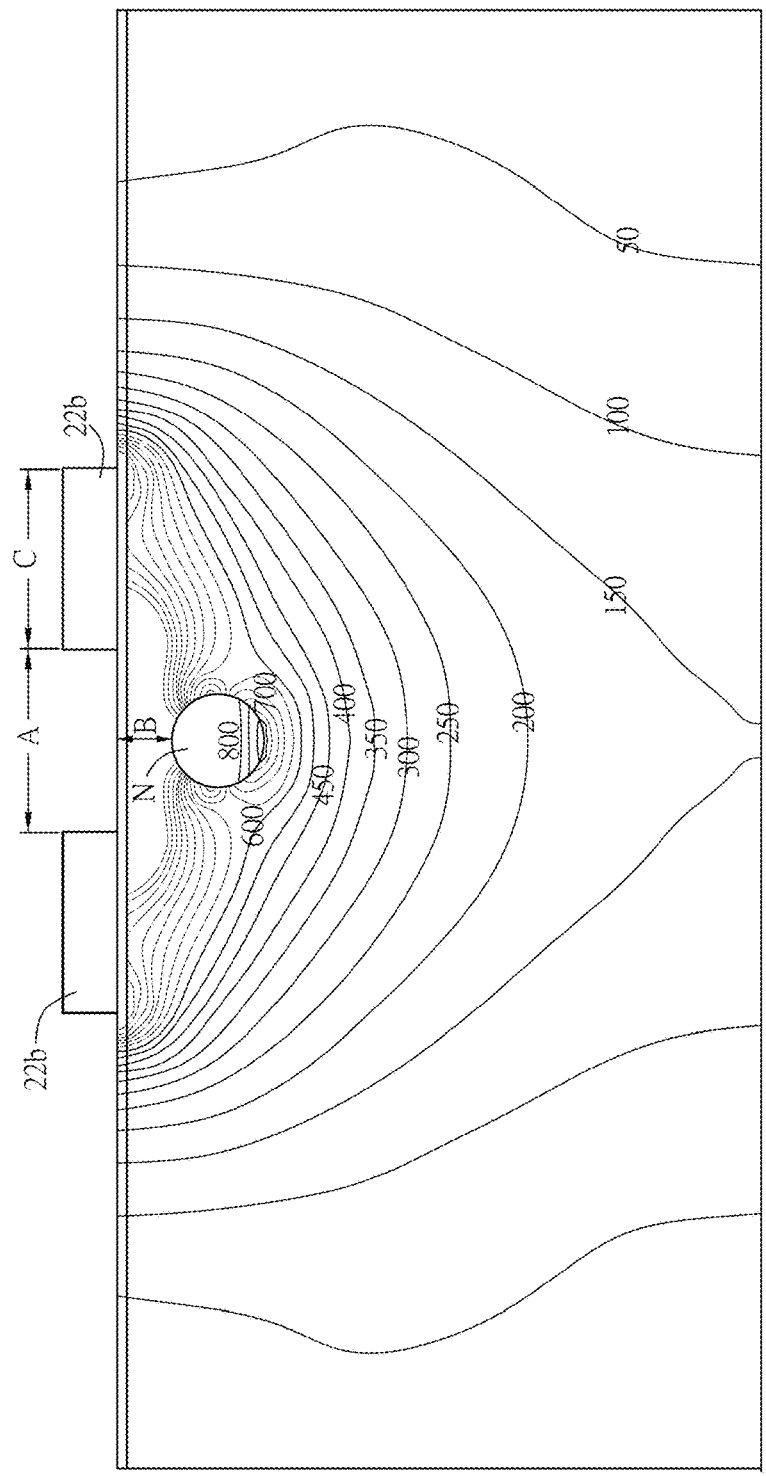

Furthermore, please refer to FIG. 16, which is yet another schematic diagram of the electric field simulation of the desensitizing device when applying on a wrist. The field pattern of the electric field is adjusted by adjusting the distance A between the electrodes 22b, the distance B between skin surface and the median nerve N (the circle portion), or the width C of the electrodes. In the simulation experiment, the voltage of the stimulating signal is 10V, the frequency of the stimulating signal is 800 KHz. As shown in the FIG. 16, within the workable distance, in the experiment the distance A=10 mm, the distance B=5 mm and the width C is 10 mm, the electric field (the strength of the electric field is 700V/m~800V/m) may only or mainly effectively cover the subcutaneous nerve N. Relatively, the electric field strength is more intense if the position is closer to the electrodes 22b.

Figure 17:
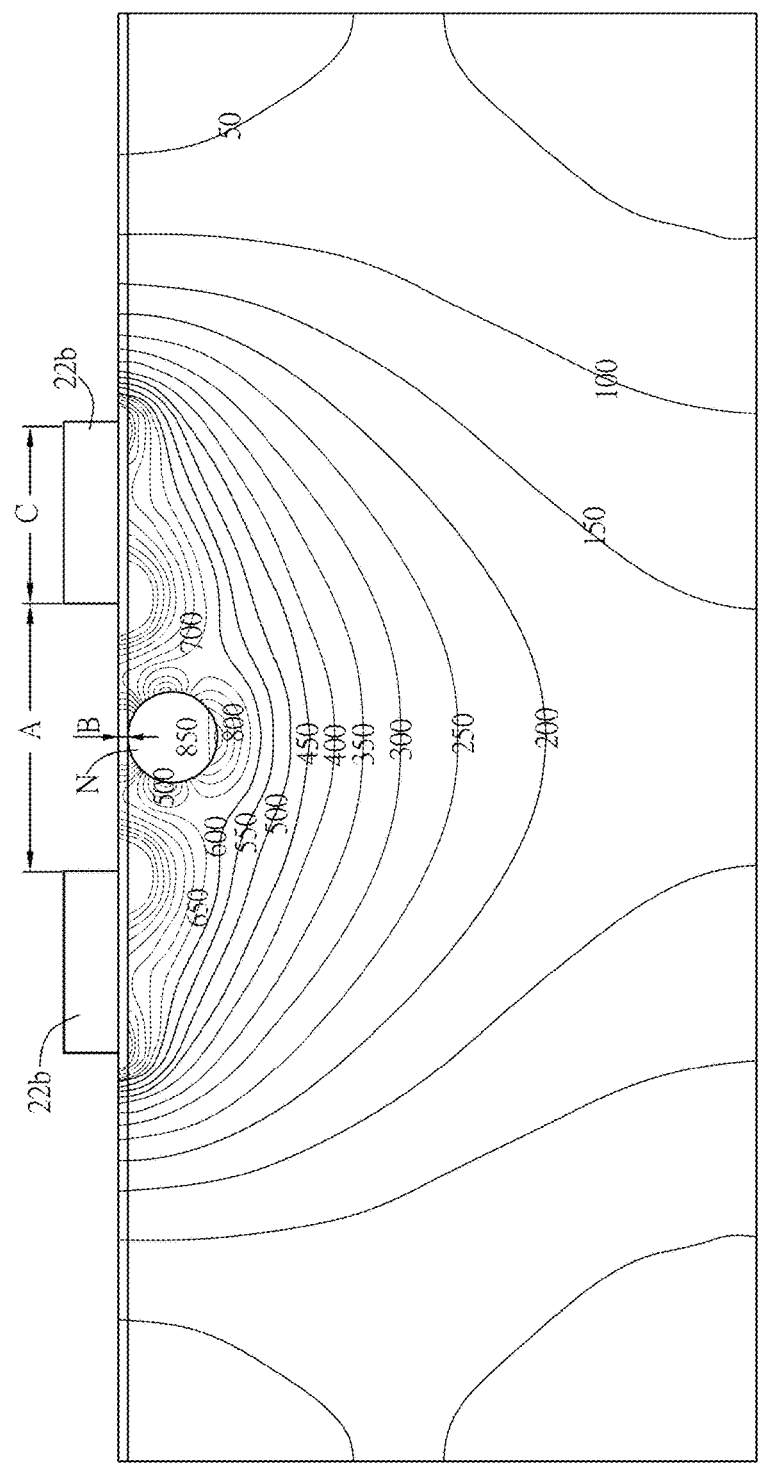

Furthermore, please refer to FIG. 17, which is yet another schematic diagram of the electric field simulation of the desensitizing device when applying on a wrist. The field pattern of the electric field is adjusted by adjusting the distance A between the electrodes 22b, the distance B between skin surface and the median nerve N (the circle portion), or the width C of the electrodes. In the simulation experiment, the voltage of the stimulating signal is 10V, the frequency of the stimulating signal is 800 KHz. As shown in the FIG. 17, within the workable distance, in the experiment the distance A=15 mm, the distance B=0 mm and the width C is 10 mm, the electric field (the strength of the electric field is 800V/m~850V/m) may only or mainly effectively cover the subcutaneous nerve N. Relatively, the electric field strength is more intense if the position is closer to the electrodes 22b.

Figure 18:
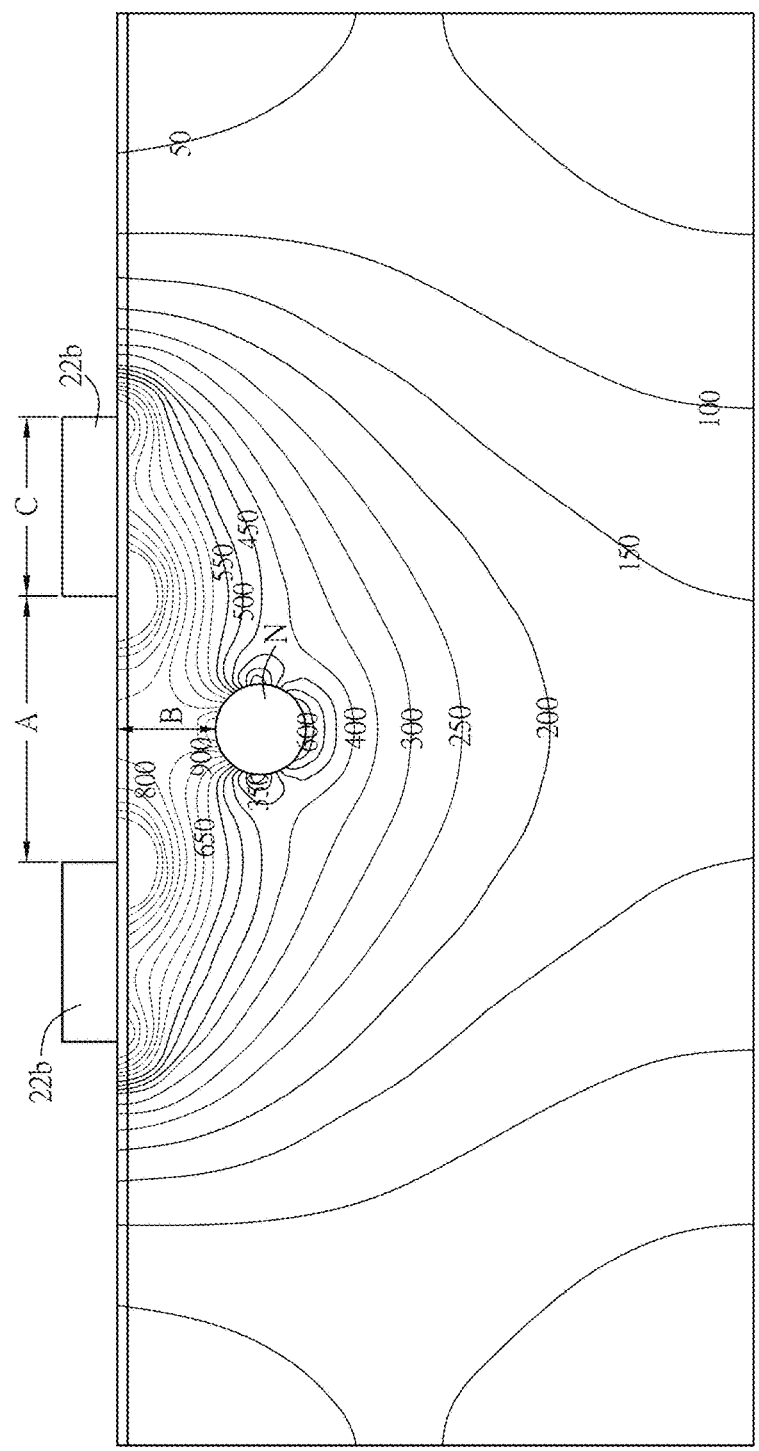

Furthermore, please refer to FIG. 18, which is yet another schematic diagram of the electric field simulation of the desensitizing device when applying on a wrist. The field pattern of the electric field is adjusted by adjusting the distance A between the electrodes 22b, the distance B between skin surface and the median nerve N (the circle portion), or the width C of the electrodes. In the simulation experiment, the voltage of the stimulating signal is 10V, the frequency of the stimulating signal is 800 KHz. As shown in the FIG. 18, within the workable distance, in the experiment the distance A=15 mm, the distance B=7.5 mm and the width C is 10 mm, the electric field (the strength of the electric field is 600V/m~900V/m) may only or mainly effectively cover the subcutaneous nerve N. Relatively, the electric field strength is more intense if the position is closer to the electrodes 22*b*.

Figure 19:
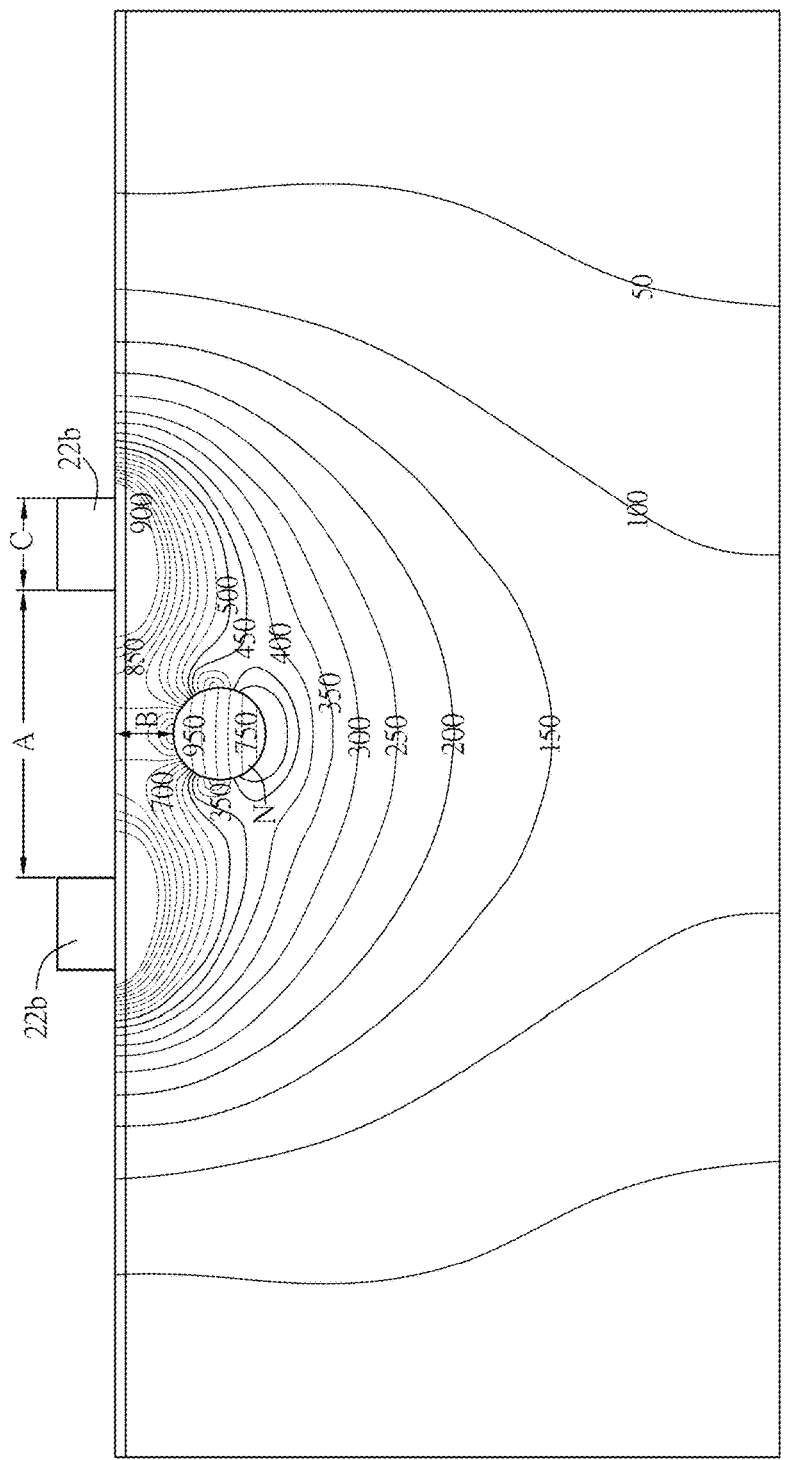

Furthermore, please refer to FIG. 19, which is yet another schematic diagram of the electric field simulation of the desensitizing device when applying on a wrist. The field pattern of the electric field is adjusted by adjusting the distance A between the electrodes 22*b*, the distance B between skin surface and the median nerve N (the circle portion), or the width C of the electrodes. In the simulation experiment, the voltage of the stimulating signal is 10V, the frequency of the stimulating signal is 800 KHz. As shown in the FIG. 19, within the workable distance, in the experiment the distance A=15 mm, the distance B=5 mm and the width C is 5 mm, the electric field (the strength of the electric field is 700V/m~950V/m) may only or mainly effectively cover the subcutaneous nerve N. Relatively, the electric field strength is more intense if the position is closer to the electrodes 22*b*.

Figure 20:
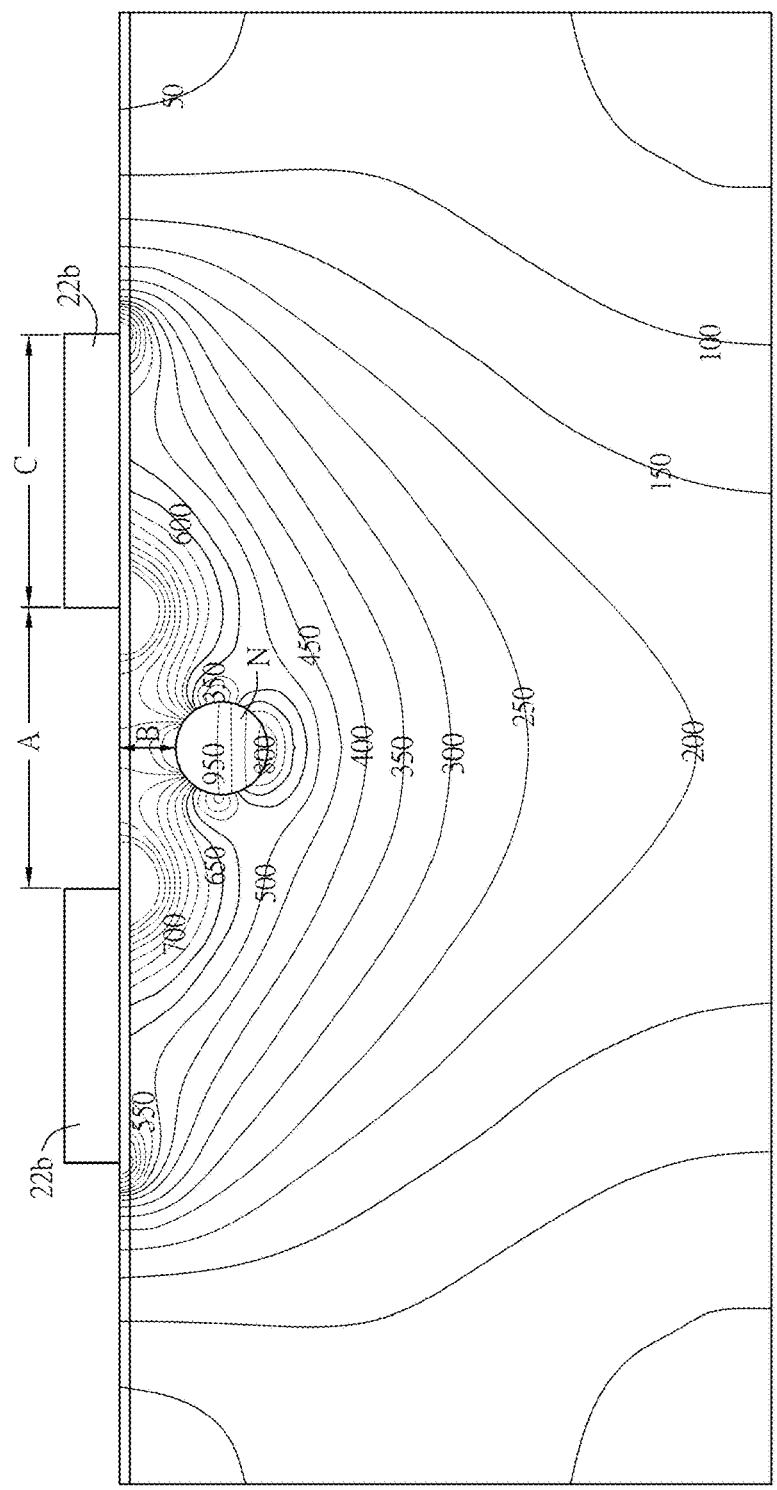

Furthermore, please refer to FIG. 20, which is yet another schematic diagram of the electric field simulation of the desensitizing device when applying on a wrist. The field pattern of the electric field is adjusted by adjusting the distance A between the electrodes 22*b*, the distance B between skin surface and the median nerve N (the circle portion), or the width C of the electrodes. In the simulation experiment, the voltage of the stimulating signal is 10V, the frequency of the stimulating signal is 800 KHz. As shown in the FIG. 20, within the workable distance, in the experiment the distance A=15 mm, the distance B=5 mm and the width C is 15 mm, the electric field (the strength of the electric field is 800V/m~950V/m) may only or mainly effectively cover the subcutaneous nerve N. Relatively, the electric field strength is more intense if the position is closer to the electrodes 22*b*.

Figure 21:
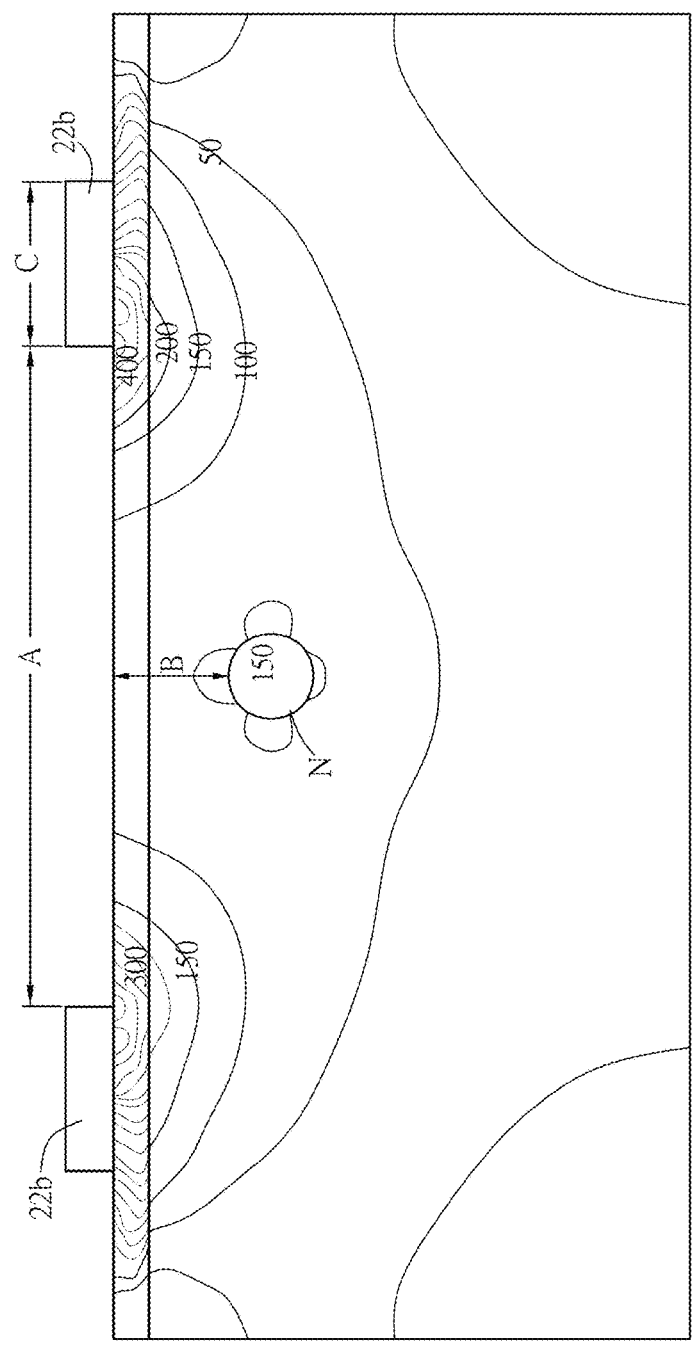

Furthermore, please refer to FIG. 21, which is yet another schematic diagram of the electric field simulation of the desensitizing device when applying on a wrist. The field pattern of the electric field is adjusted by adjusting the distance A between the electrodes 22*b*, the distance B between skin surface and the median nerve N (the circle portion), or the width C of the electrodes. In the simulation experiment, the voltage of the stimulating signal is 5V, the frequency of the stimulating signal is 500 KHz. As shown in the FIG. 21, within the workable distance, in the experiment the distance A=40 mm, the distance B=7.5 mm and the width C is 10 mm, the electric field (the strength of the electric field is 100V/m~150V/m) may only or mainly effectively cover the subcutaneous nerve N. Relatively, the electric field strength is more intense if the position is closer to the electrodes 22*b*.

Figure 22:
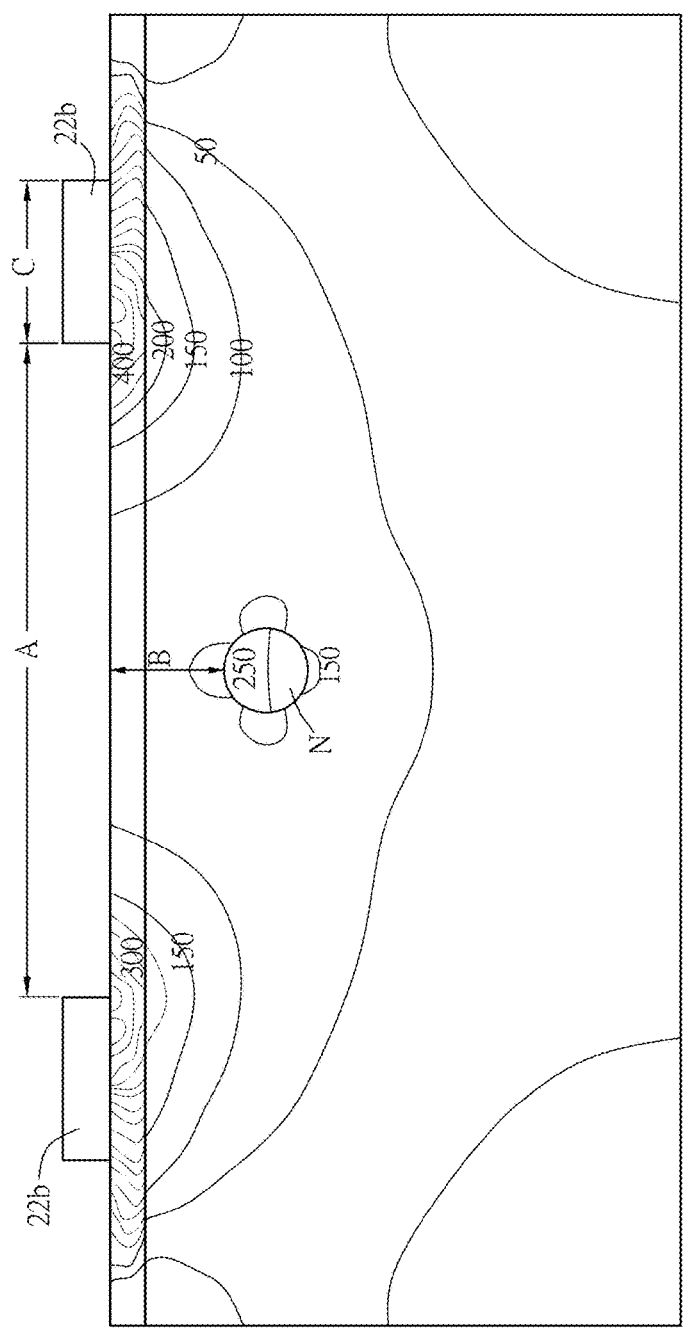

Furthermore, please refer to FIG. 22, which is yet another schematic diagram of the electric field simulation of the desensitizing device when applying on a wrist. The field pattern of the electric field is adjusted by adjusting the distance A between the electrodes 22*b*, the distance B between skin surface and the median nerve N (the circle portion), or the width C of the electrodes. In the simulation experiment, the voltage of the stimulating signal is 5V, the frequency of the stimulating signal is 500 KHz. As shown in the FIG. 22, within the workable distance, in the experiment the distance A=40 mm, the distance B=5 mm and the width C is 10 mm, the electric field (the strength of the electric field is 150V/m~250V/m) may only or mainly effectively cover the subcutaneous nerve N. Relatively, the electric field strength is more intense if the position is closer to the electrodes 22*b*.

Figure 23:
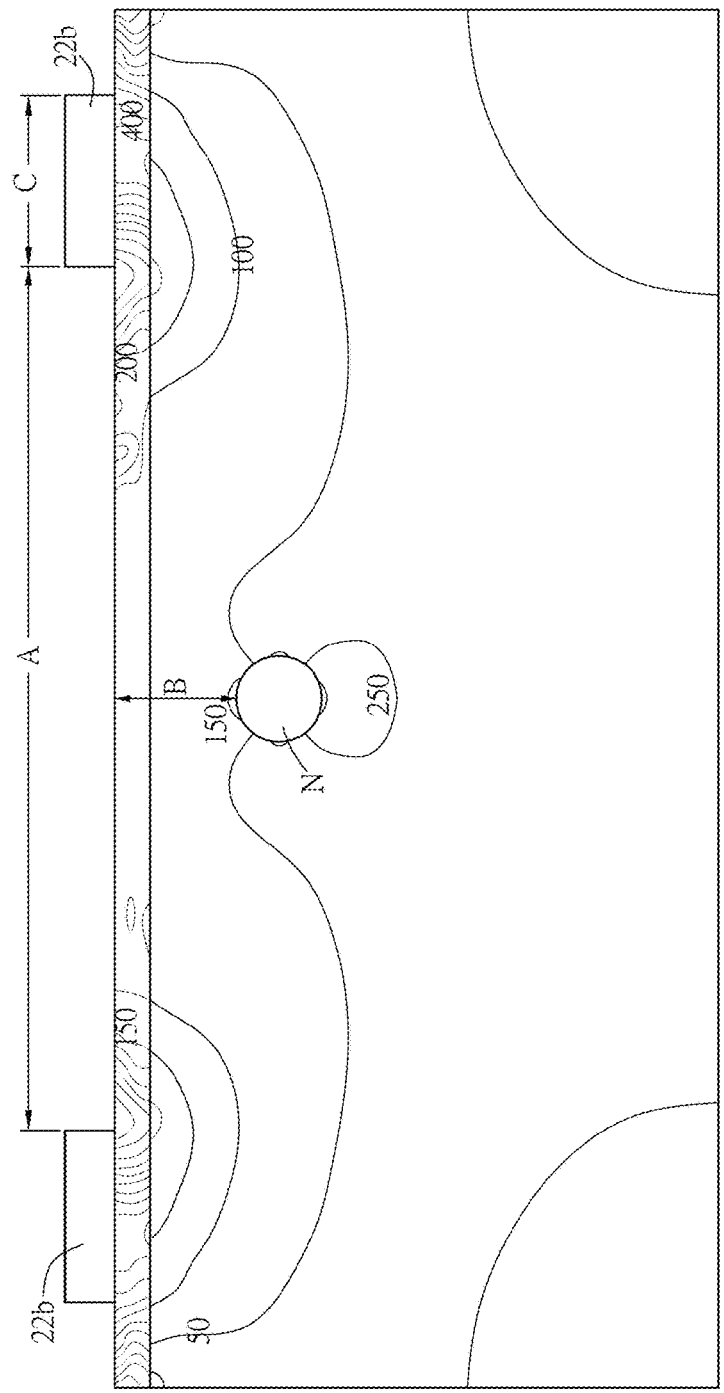

Furthermore, please refer to FIG. 23, which is yet another schematic diagram of the electric field simulation of the desensitizing device when applying on a wrist. The field pattern of the electric field is adjusted by adjusting the distance A between the electrodes 22*b*, the distance B between skin surface and the median nerve N (the circle portion), or the width C of the electrodes. In the simulation experiment, the voltage of the stimulating signal is 5V, the frequency of the stimulating signal is 500 KHz. As shown in the FIG. 23, within the workable distance, in the experiment the distance A=50 mm, the distance B=5 mm and the width C is 10 mm, the electric field (the strength of the electric field is 150V/m~250V/m) may only or mainly effectively cover the subcutaneous nerve N. Relatively, the electric field strength is more intense if the position is closer to the electrodes 22*b*.

Figure 24:
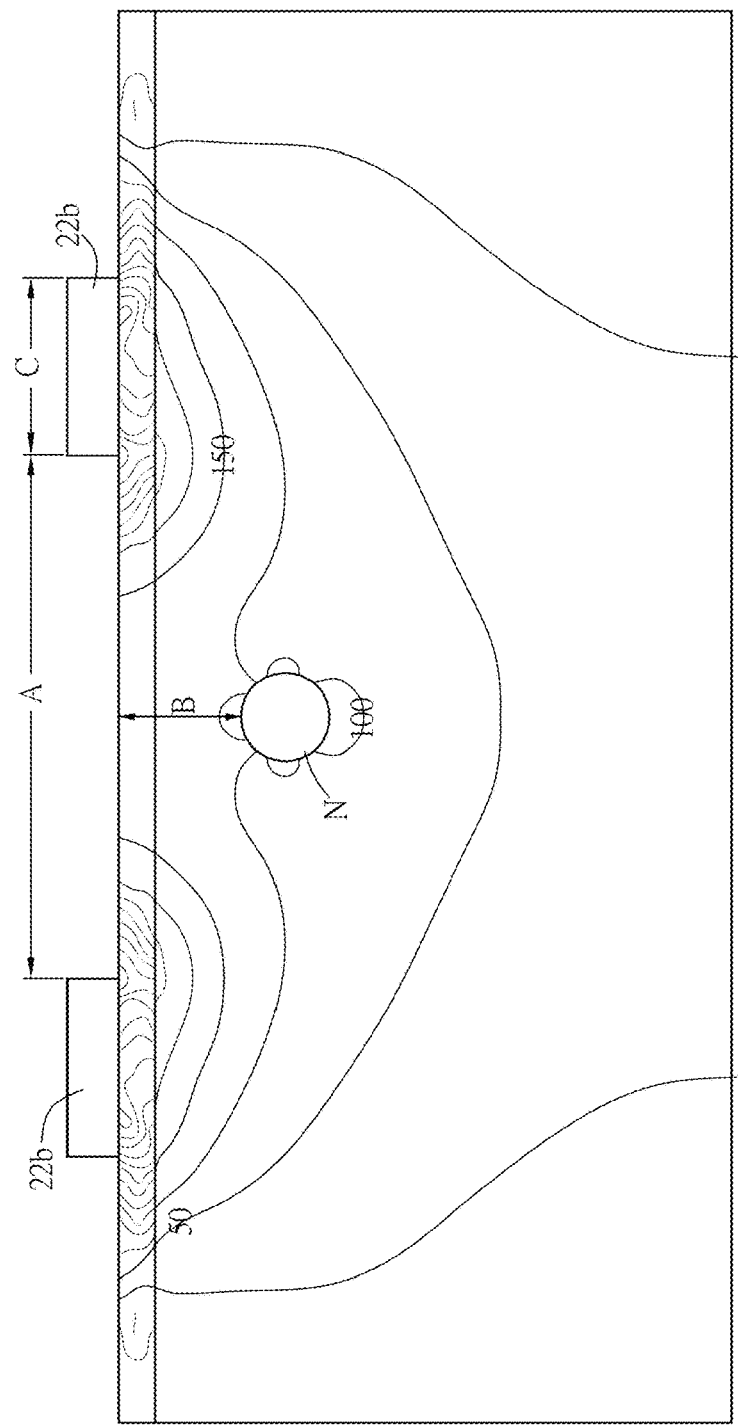

Furthermore, please refer to FIG. 24, which is yet another schematic diagram of the electric field simulation of the desensitizing device when applying on a wrist. The field pattern of the electric field is adjusted by adjusting the distance A between the electrodes 22*b*, the distance B between skin surface and the median nerve N (the circle portion), or the width C of the electrodes. In the simulation experiment, the voltage of the stimulating signal is 5V, the frequency of the stimulating signal is 500 KHz. As shown in the FIG. 24, within the workable distance, in the experiment the distance A=30 mm, the distance B=5 mm and the width C is 10 mm, the electric field (the strength of the electric field is 100V/m~150V/m) may only or mainly effectively cover the subcutaneous nerve N. Relatively, the electric field strength is more intense if the position is closer to the electrodes 22*b*.

Figure 25:
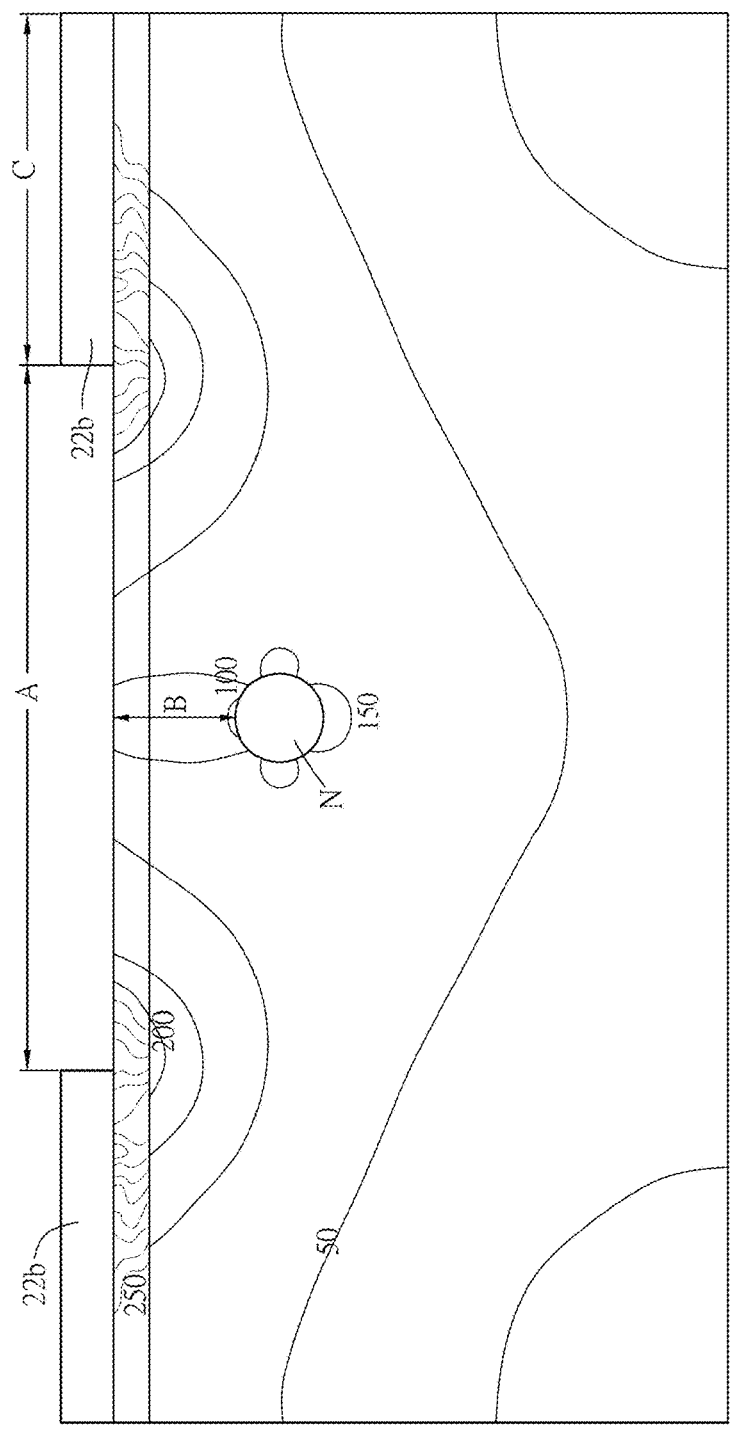

Furthermore, please refer to FIG. 25, which is yet another schematic diagram of the electric field simulation of the desensitizing device when applying on a wrist. The field pattern of the electric field is adjusted by adjusting the distance A between the electrodes 22*b*, the distance B between skin surface and the median nerve N (the circle portion), or the width C of the electrodes. In the simulation experiment, the voltage of the stimulating signal is 5V, the frequency of the stimulating signal is 500 KHz. As shown in the FIG. 25, within the workable distance, in the experiment the distance A=40 mm, the distance B=5 mm and the width C is 20 mm, the electric field (the strength of the electric field is 100V/m~150V/m) may only or mainly effectively cover the subcutaneous nerve N. Relatively, the electric field strength is more intense if the position is closer to the electrodes 22*b*.

Figure 26:
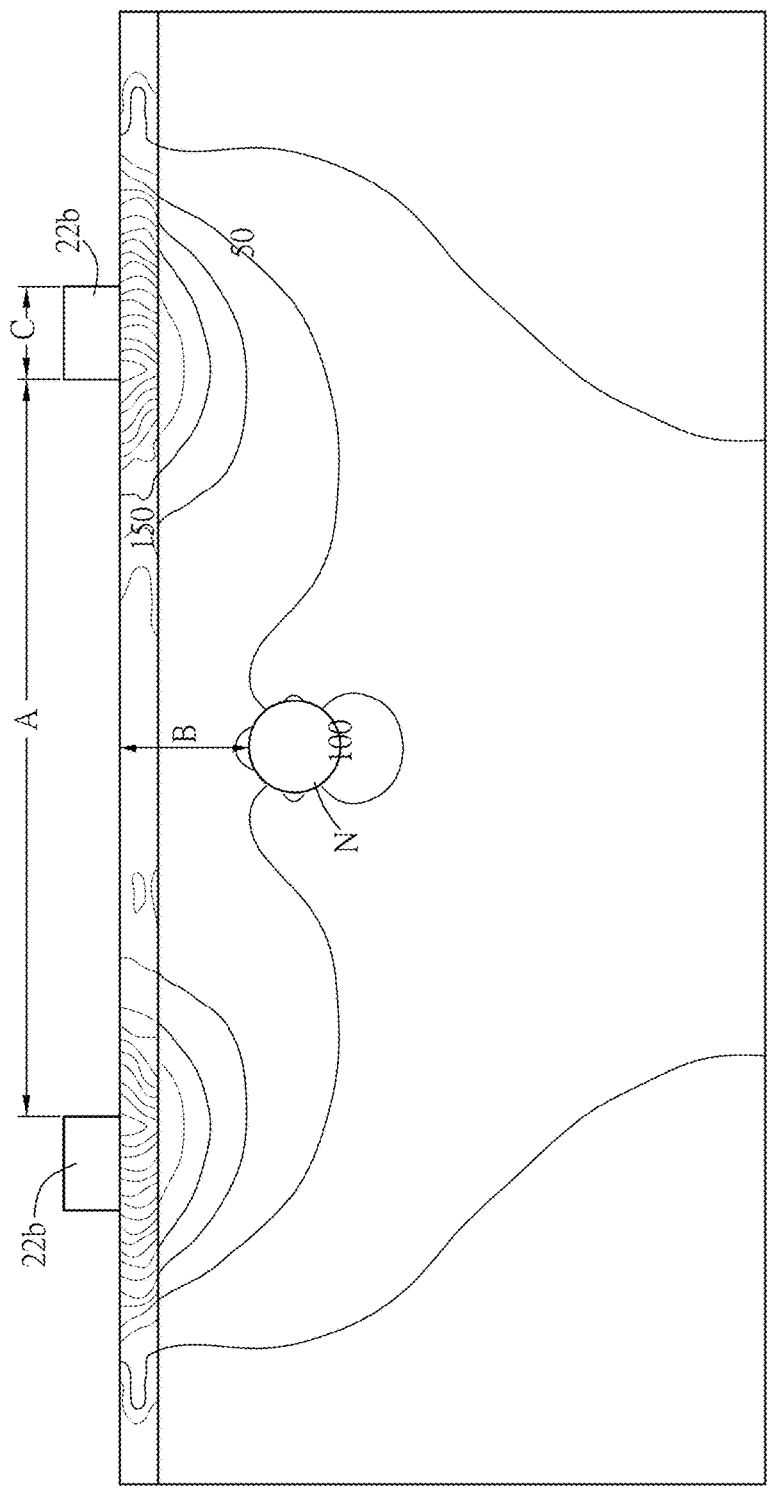

Furthermore, please refer to FIG. 26, which is yet another schematic diagram of the electric field simulation of the desensitizing device when applying on a wrist. The field pattern of the electric field is adjusted by adjusting the distance A between the electrodes 22*b*, the distance B between skin surface and the median nerve N (the circle portion), or the width C of the electrodes. In the simulation experiment, the voltage of the stimulating signal is 5V, the frequency of the stimulating signal is 500 KHz. As shown in the FIG. 26, within the workable distance, in the experiment the distance A=40 mm, the distance B=5 mm and the width C is 5 mm, the electric field (the strength of the electric field is 100V/m~150V/m) may only or mainly effectively cover the subcutaneous nerve N. Relatively, the electric field strength is more intense if the position is closer to the electrodes 22b.

The present invention also provides a desensitizing method for the above-mentioned desensitizing device. Those skilled in the art should be readily understand the process of the desensitizing method by reading the description of operations of the desensitizing device according to the embodiments of the present invention, and thereby the details of the desensitizing method are omitted here for brevity.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

What is claimed is:

1. A desensitizing device, comprising an electrical stimulation member; wherein the electrical stimulation member comprises:
    a controller producing a stimulating signal, wherein the simulating signal is a pulse signal and its pulse repetition frequency is between 0 to 1 KHz;
    at least two electrodes configured to be attached to a user's skin and electrically connected to the controller to receive the stimulating signal from the controller and to apply the stimulating signal to a subcutaneous nerve via the skin, wherein the stimulating signal makes the at least two electrodes generate an electric field at least partially covering the subcutaneous nerve, and the magnitude of the electric field ranges from 100 V/m to 1000 V/m such that when the simulating signal is applied, the subcutaneous nerve is temporarily desensitized; and
    a support member having an outer circumference, an inner circumference, a through channel surrounded by the inner circumference, and an accommodation space with a first opening on the outer circumference and at least two second openings on the inner circumference.

2. The desensitizing device according to claim 1, wherein the stimulating signal has a frequency between 200 KHz and 800 KHz.

3. The desensitizing device according to claim 2, wherein the frequency of the stimulating signal ranges from 200 KHz to 450 KHz, or ranges from 450KHz to 550KHz, or ranges from 550 KHz to 800 KHz.

4. The desensitizing device according to claim 1, wherein the voltage of the stimulating signal ranges from −10V to −1V or ranges from 1V to 10V.

5. The desensitizing device according to claim 1, wherein the current of the stimulating signal ranges from 2 mA to 50 mA.

6. The desensitizing device according to claim 1, wherein the stimulation signal is adapted to block the neurotransmission of the subcutaneous nerve.

7. The desensitizing device according to claim 1, wherein the subcutaneous nerve is under the skin of a penis, a wrist, an elbow, or a head.

8. The desensitizing device according to claim 1, wherein the at least two electrodes are exposed from the inner circumference through the second openings, respectively.

9. The desensitizing device according to claim 1, wherein the at least two electrodes are flexible pads.

10. The desensitizing device according to claim 1, further comprising a support member; wherein the support member is belt-shaped or a substantially ring-like shape.

11. The desensitizing device according to claim 1, wherein the electrodes are extended from the controller by a plurality of transmission wires, respectively.

12. The desensitizing device according to claim 1, further comprising a power supply unit.

13. The desensitizing device according to claim 12, wherein the power supply unit comprises a removable battery.

14. The desensitizing device according to claim 12, wherein the power supply unit comprises a built-in rechargeable battery.

15. A desensitizing method for a desensitizing device having a controller configured to produce a stimulating signal, and at least two electrodes configured to be attached to a user's skin and electrically connected to the controller, the desensitizing method comprises steps of:
    producing a stimulating signal using the controller;
    receiving the stimulating signal by the at least two electrodes; and
    applying the stimulating signal to a subcutaneous nerve via the skin, wherein the simulating signal is a pulse signal and its pulse repetition frequency is between 0 to 1 KHz; and
    wherein the stimulating signal makes the at least two electrodes generate an electric field at least partially covering the subcutaneous nerve, and the magnitude of the electric field ranges from 100 V/m to 1000 V/m such that when the simulating signal is applied, the subcutaneous nerve is temporarily desensitized, and the desensitizing device further comprises a support member having an outer circumference, an inner circumference, a through channel surrounded by the inner circumference, and an accommodation space with a first opening on the outer circumference and at least two second openings on the inner circumference.

16. The desensitizing method of claim 15, wherein the stimulating signal has a frequency between 200 KHz and 800 KHz.

17. The desensitizing method according to claim 15, wherein the voltage of the stimulating signal ranges from −10V to −1V or ranges from 1V to 10y, and the current of the stimulating signal ranges from 2 mA to 50 mA.

* * * * *